US007807644B2

(12) United States Patent
Lind et al.

(10) Patent No.: US 7,807,644 B2
(45) **Date of Patent: *Oct. 5, 2010**

(54) CHIMERIC PROTEINS WITH PHOSPHATIDYLSERINE BINDING DOMAINS

(75) Inventors: Stuart E. Lind, Oklahoma City, OK (US); Wei-Qun Ding, Edmond, OK (US); Roger G. Harrison, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/157,525

(22) Filed: Jun. 11, 2008

(65) Prior Publication Data

US 2008/0280831 A1 Nov. 13, 2008

Related U.S. Application Data

(63) Continuation of application No. 11/371,872, filed on Mar. 8, 2006, now Pat. No. 7,393,833.

(60) Provisional application No. 60/659,938, filed on Mar. 9, 2005.

(51) Int. Cl.
*A61K 38/00* (2006.01)

(52) U.S. Cl. ........................................................ 514/12

(58) Field of Classification Search .................... 514/12
See application file for complete search history.

(56) References Cited

U.S. PATENT DOCUMENTS

| | | | |
|---|---|---|---|
| 5,296,467 | A | 3/1994 | Reutelingsperger |
| 5,298,599 | A | 3/1994 | Rezaie et al. |
| 6,132,729 | A | 10/2000 | Thorpe et al. |
| 6,156,321 | A | 12/2000 | Thorpe et al. |
| 6,194,214 | B1 | 2/2001 | Kraus |
| 6,312,694 | B1 | 11/2001 | Thorpe et al. |
| 6,406,693 | B1 | 6/2002 | Thorpe et al. |
| 6,491,894 | B1 | 12/2002 | Ruoslahti et al. |
| 6,528,481 | B1 | 3/2003 | Burg et al. |
| 6,576,239 | B1 | 6/2003 | Ruoslahti et al. |
| 6,610,651 | B1 | 8/2003 | Ruoslahti et al. |
| 6,749,853 | B1 | 6/2004 | Thorpe et al. |
| 6,818,213 | B1 | 11/2004 | Thorpe et al. |
| 6,933,281 | B2 | 8/2005 | Ruoslahti et al. |
| 6,962,903 | B2 | 11/2005 | Allison |
| 7,252,959 | B2 | 8/2007 | Rand |
| 7,393,833 | B2 * | 7/2008 | Lind et al. .................... 514/12 |

FOREIGN PATENT DOCUMENTS

WO WO 2000/02587 1/2000

OTHER PUBLICATIONS

Huang et al., "A soluble tissue factor-annexin V chimeric protein has both procoagulant and anticoagulant properties", *Blood*, vol. 107, No. 3, pp. 980-986 (Feb. 1, 2006).

Paborsky et al., "Lipid Association, but Not the Transmembrane Domain, Is Required for Tissue Factor Activity", *The Journal of Biological Chemistry*, vol. 266, No. 32, pp. 21911-21916 (Nov. 15, 1991).

Ida et al., "Human Annexin V Binds to Sulfatide: Contribution to Regulation of Blood Coagulation", *Journal of Biochemistry*, (2004), vol. 135, No. 5, pp. 583-588, [ http://jb.oxfordjournals.org ] (3 pages).

Rand et al., "Human Monoclonal Antiphospholipid Antibodies Disrupt the Annexin A5 Anticoagulant Crystal Shield on Phospholipid Bilayers", *American Journal of Pathology*, vol. 163, No. 3 (Sep. 2003) pp. 1193-1200.

Thiagarajan et al., "Inhibition of Arterial Thrombosis by Recombinant Annexin V in a Rabbit Carotid Artery Injury Model", *Circulation*, (1997) vol. 96, pp. 2339-2347 [ http://www.circ.ahajournals.org ] (23 pages).

Wang et al., "Ligand-regulated secretion of recombinant annexin V from cultured thyroid epithelial cells", *Am. J. Physiol. Cell. Physiol.* (2002) vol. 282, pp. C1313-C1321 [ http://ajpcell.physiology.org ] (14 pages).

"Annexin A5" [ http://en.wikipedia.org/wiki/Annexin_A5 ] (4 pages), Dec. 2007.

Abnova® Corporation, [ http://www.abnova.com. ] (2 pages), Dec. 2007.

Chen et al., "Fusion proteins comprising annexin V and Kunitz protease inhibitors are highly potent thrombogenic site-directed anticoagulants", Blood, (May 15, 2005), vol. 105, No. 10, pp. 3902-3909, [http://bloodjournal.hematologylibrary.org] (15 pages).

* cited by examiner

*Primary Examiner*—Maryam Monshipouri
(74) *Attorney, Agent, or Firm*—Dunlap Codding, PC

(57) ABSTRACT

Chimeric proteins comprising soluble Tissue Factor (sTF) and another subunit (e.g., annexin V) are described. The proteins promote blood clotting and/or inhibit cancer by targeting sTF to specific receptors such as phosphatidylserine (PS) on activated cells. These chimeric proteins are useful in treating patients with excessive bleeding due to inborn problems, drug therapy, trauma or surgery and/or as an anti-cancer therapy, for example by causing blood vessels feeding cancers to become clotted, thereby preventing adequate flow of blood to a tumor, which in turn will lead to tumor inhibition and death or may be used in a therapy to cause clotting within blood vessels that pose a threat in the subject in non-cancerous conditions.

13 Claims, 8 Drawing Sheets

CHIMERIC PROTEINS WITH PHOSPHATIDYLSERINE BINDING DOMAINS

CROSS-REFERENCE TO RELATED APPLICATIONS

This application is a continuation of U.S. Ser. No. 11/371,872, filed Mar. 8, 2006, now U.S. Pat. No. 7,393,833, which claims the benefit under 35 U.S.C. 119(e) of U.S. Provisional Application Ser. No. 60/659,938, filed Mar. 9, 2005, the entireties, of each of which are hereby expressly incorporated herein by reference.

STATEMENT REGARDING FEDERALLY SPONSORED RESEARCH OR DEVELOPMENT

Not applicable.

BACKGROUND OF THE INVENTION

Hemostasis (the process of initiating blood coagulation in order to stop bleeding) may be abnormal and possibly life-threatening under a number of circumstances, yet there is a need for improved methods of inducing hemostasis under special conditions. Hemostasis is initiated by platelets, which are blood cells that cause occlusion of holes in blood vessels. In the course of doing so, platelets become "activated". One aspect of their activation is the translocation of phosphatidylserine (PS) from the inner half of their plasma membrane to the outer half. Once this occurs, certain blood coagulation proteins bind to the surface of the platelet and interact in the process known as "blood coagulation". The end result of that process is the formation of the enzyme thrombin (also called Factor IIa). Thrombin has several important roles. First, it converts the blood protein fibrinogen into fibrin. Each fibrin binds to several other fibrin molecules, forming a fibrin clot, which supports the platelets that are attempting to stop bleeding. Second, thrombin also activates platelets, increasing the number involved in the hemostatic process. And third, thrombin affects other plasma proteins, such as Factor XI, in a manner that accelerates the biochemistry of blood coagulation. The first proteins that interact on the surface of platelets (or other cells with exposed PS) are Tissue Factor (TF), the activated form of Factor VII (called Factor VIIa), and Factor X.

Thrombin generation is initiated by the interaction of the plasma serine protease, Factor VIIa, with its protein cofactor, TF. TF is a membrane-bound protein not expressed on the surface of cells in contact with the bloodstream until they become activated. Upon its expression, TF binds either Factor VII (promoting its activation to Factor VIIa), or Factor VIIa, increasing its catalytic efficiency in converting Factor X to Factor Xa. Expression of the extracellular domain of TF (amino acids 1-219, or a 3-219 residue portion of the entire protein) in *E. coli* generates a polypeptide of about 26 kDa that retains the ability to bind to Factor VIIa and to allosterically activate it. This truncated TF (called soluble TF or sTF) does not bind to cellular membranes and is therefore generally much less efficient than native TF in promoting Factor VII autoactivation or activation of Factor X by Factor VIIa. Engineering of the cDNA encoding sTF so that it was expressed on the surface of mammalian cells as a glycosylphosphatidylinositol-anchored protein resulted in a protein with the same specific procoagulant activity as native TF, underscoring the importance of membrane attachment for this protein.

It has long been recognized that congenital Factor VIII deficiency is characterized by abnormal thrombin generation when blood coagulation is triggered by low concentrations of TF. More recently recognized is the fact that disorders of platelet function are also associated with decreased thrombin generation. The vitamin K-dependent blood coagulation proteins, which are required for thrombin generation, assemble on the surface of activated platelets, endothelial cells, and/or monocytes by binding to anionic phospholipids, especially PS. Thrombin, a potent platelet agonist, amplifies the activation of platelets initiated by contact with sub-endothelial collagen exposure. Delayed thrombin generation may therefore underlie or amplify the bleeding tendency accompanying disorders of plasma coagulation factors, or blood platelets.

Others have reported that the intravenous injection of thromboplastin (membrane-bound TF) into animals results in generalized activation of the coagulation, as does injection of both sTF and Factor VIIa, resulting in beneficial effects upon bleeding in experimental animals, suggesting that sTF might serve as the basis of a therapy designed to reduce bleeding.

A therapeutic protein effective in enhancing hemostasis and coagulation in a subject in need thereof would be desirable.

DETAILED DESCRIPTION OF THE INVENTION

Figure 1:
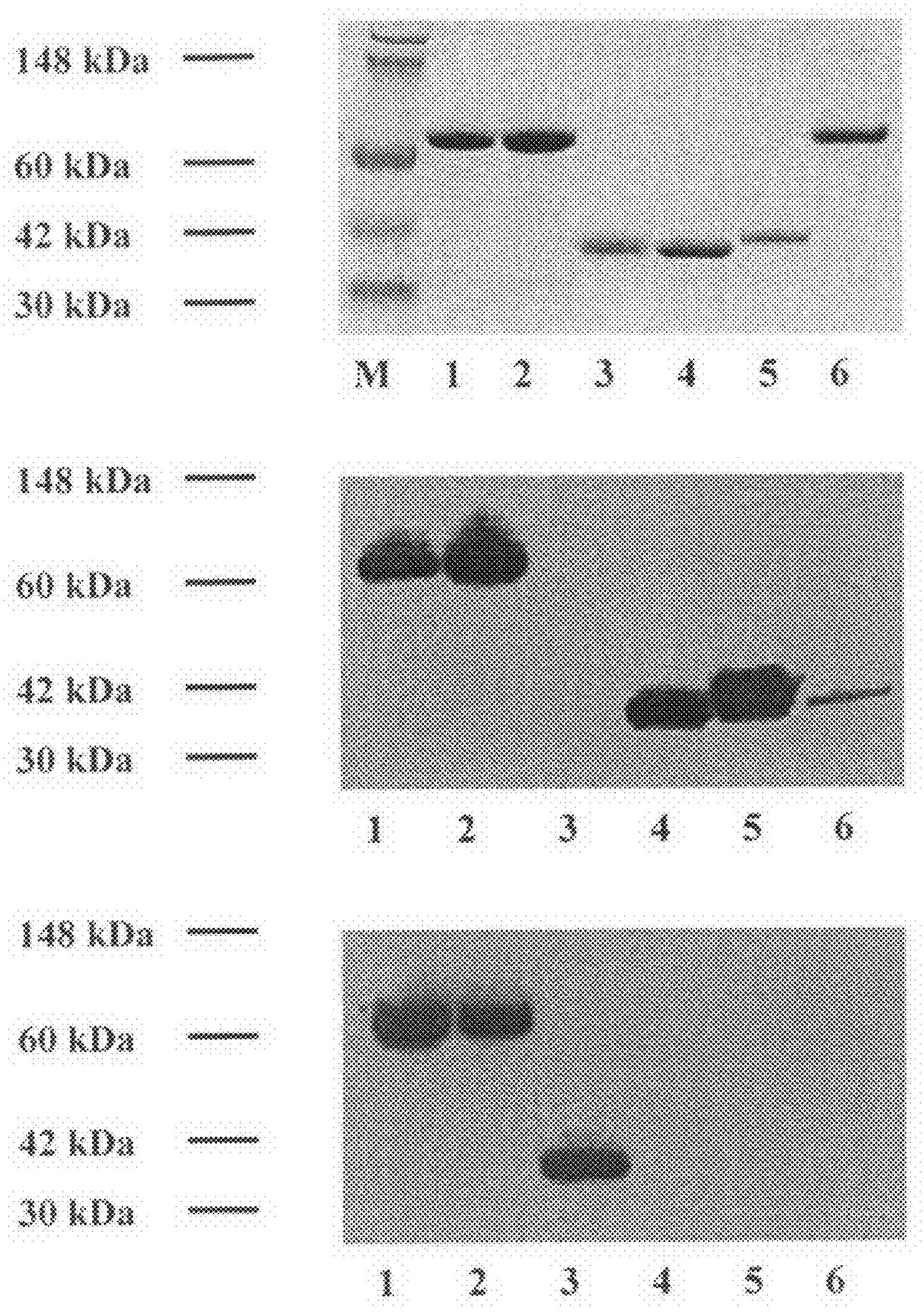
FIG. 1. Protein purification and western blotting of recombinant proteins. Top, SDS-PAGE and Coomassie blue staining. Middle, Western blot using a mouse monoclonal antibody to human TF. Bottom, Western blot using mouse monoclonal antibody to $His_6$. M, molecule weight marker; Lanes 1-5 are identical in panels A, B, and C: lane 1, sTF-annexin V (sTF-annV); lane 2, sTFAA-annexin V (sTFM-annV); lane 3, annexin V; lane 4, sTF; lane 5, recombinant TF. Lane 6, panel A: bovine serum albumin; panel B: recombinant TF (Innovin®, Dade Behring, Newark, Del.).

The present invention contemplates delivering chimeric proteins comprising soluble Tissue Factor (sTF), or effective portions thereof having activity sufficient to enhance anidolytic activity of Factor VIIa by at least 10-fold, to sites of vascular injury where they function as a hemostatic agent while minimizing the chance of inducing disseminated intravascular coagulation (DIC). Although targeting might be undertaken by using an antibody specific for activated platelets, endothelial cells or monocytes, a targeting moiety capable of binding to all three cell types would be preferable, insofar as it would be less sensitive to alterations in the number of targeted cells that might be present in any given individual. Since each of the cell types of interest expresses phosphatidylserine (PS) on its surface when activated, the present invention contemplates a sTF chimeric protein (e.g., sTF-annV) for use in targeting sTF to PS-containing membranes wherein the sTF is coupled to a PS-binding domain such as annexin V (AnnV), a human PS-binding protein which has been shown to bind to activated platelets, endothelial cells and monocytes. Arguing against the use of annexin V in this manner was the fact that it is an anticoagulant protein, due to its ability to compete with vitamin K-dependent proteins for binding to PS-containing membranes.

In a preferred embodiment of the invention, sTF comprises 217 amino acids (SEQ ID NO:2) of the human TF attached to the amino terminus of AnnV, (it may also be attached to the carboxy terminus, and may be linked to the amino terminus or carboxy terminus via a linker sequence). As noted before, TF is normally bound to cell membranes because it contains an intramembraneous anchoring region, However, sTF, which lacks the anchoring region and was cloned and expressed over 10 years ago, is approximately 1000-fold less active than the native protein (TF). sTF is encoded for example by a cDNA comprising SEQ ID NO:1.

Soluble Tissue Factor (sTF) as contemplated herein comprises SEQ ID NO:2, or any subsequence thereof having a cysteine in position 207 and which retains activity sufficient to enhance the amidolytic activity of Factor VIIa by at least 10 fold. Thus the sTF contemplated for use herein may comprise a truncated portion of sTF comprising amino acids 1-207, 5-207, 10-207, 15-207, 20-207, 25-207, 30-207, 35-207, 40-207, 45-207, 50-207, 55-207, 60-207, 65-207, 70-207, 75-207, 80-207, 85-207, 90-207, 95-207, 100-207, or 105-207 and all sequences inclusive between 1-207 and 105-207, including for example 2-207 and 104-207. The invention further comprises any alternative cDNA which encodes SEQ ID NO:2 or a functionally active truncated portion thereof as described herein, for example the alternative cDNA which encodes SEQ ID NO:2 may comprise a cDNA similar to SEQ ID NO:1 but which has conservatively substituted codons (i.e., a coding having a different nucleotide sequence but which encodes the same amino acid).

The invention further comprises any of the sTF sequences or truncated sequences as described herein which further comprises an additional ser-gly sequence or just a gly residue on the N-terminal portion of SEQ ID NO:2, thereby providing a 219, or 218 amino acid sequence, respectively, and wherein the cysteine residue at position 207 of SEQ ID NO:2 is thus shifted to position 209, or 208, respectively.

The second domain of the sTF-AnnV chimeric protein is comprised of the entire human protein, Annexin V (SEQ ID NO:4) or of an effective PS-binding portion thereof. AnnV is a 35 kDa protein encoded for example by SEQ ID NO:3 and is produced in many cells and binds to certain phospholipids, notably phosphatidylserine as noted above. PS is normally found on the inner half of the plasma membrane (of all cells). Enzymatic mechanisms exist that can translocate PS to the outer half of the plasma membrane, where it may be bound by AnnV in the presence of calcium.

A linker region (such as, but not limited to, SEQ ID NO:6, as encoded by the cDNA having SEQ ID NO:5) is optionally present in the chimeric protein between the sTF domain and the AnnV domain. In another embodiment, the chimeric protein of the present invention may also have a non-functional tag sequence at the carboxy and/or amino terminus, or internally, and which primarily comprises for example 6-histidines (SEQ ID NO:8, as encoded by a cDNA having SEQ ID NO:7), which is used to benefit purification of the chimeric protein, and which preferably is excised therefrom prior to use of the chimeric protein in therapeutic administration.

In an alternate embodiment, a mutant form of sTF is used in the chimeric protein. In one embodiment, the sTF mutant has alanine residues at positions 163 and 164 rather than the lysine residues found at those positions in the native sTF (or in positions 165 and 166 of the sTF having 219 amino acids, for example). This alternate embodiment is referred to herein as "sTFAA-AnnV" (SEQ ID NO:10, encoded for example by a cDNA having SEQ ID NO:9). In two other embodiments, sTF mutants have glutamic acid residues or glutamine residues as substitutions at the 163 and 164 positions referred to herein as "sTFEE" (SEQ ID NO:12 as encoded for example by a cDNA having SEQ ID NO:11) and "sTFQQ" (SEQ ID NO:14 as encoded for example by a cDNA having SEQ ID NO:13, respectively). Each of these mutants or the original sTF, may include (but are not limited to) any or all of the following substitutions: ala at position 13, 131, 163, 164 or 183, asn at position 42 or 138, trp at position 48, ser at position 52, asp at position 128, glu at position 163 or 164, or gin at position 129, 163 or 164.

In fact, the present invention contemplates that at any of these positions, non-polar amino acids may be substituted with polar amino acids, or other non-polar amino acids, polar amino acids may be replaced with non-polar amino acids of other polar amino acids, positively charged amino acids may be replaced with negatively charged, polar or non-polar amino acids, or other positively charged amino acids, and negatively charged amino acids may be replaced with positively charged, polar or non-polar amino acids, or other negatively charged amino acids.

The chimeric protein sTF-annV of the present invention therefore preferably comprises, for example a protein comprising SEQ ID NO:2 or an effective portion thereof linked with a protein comprising SEQ ID NO:4 or an effective portion thereof. The sTF-annV protein may further comprise a linker, including but not limited to, a linker having SEQ ID NO:6 positioned between the sTF and annV sequences. The sTF-annV protein, with or without the linker sequence, may comprise an internal or external tag sequence such as SEQ ID NO:8 for aiding in purification of the sTF-annV protein. Any other effective linker sequence and/or purification tag sequence may be used in lieu of SEQ ID NO:6 and/or SEQ ID NO:8.

In some embodiments of the invention it may be desirable for the chimeric protein to have a shortened serum half-live to minimize the serum residence time to limit the potential for the chimeric protein to cause unwanted thrombosis, or so that the chimeric protein is eliminated after a particular amount of thrombin has been formed. In these embodiments of the invention, a cleavage site, such as a plasmin cleavage site or thrombin cleavage site can be positioned between the sTF and annV sequences of any of the chimeric proteins described herein. For example, a plasmin cleavage site having SEQ ID NO:16 (as encoded for example by a cNDN having SEQ ID NO:15), or a thrombin cleavage site such as SEQ ID NO:18 (as encoded for example, by a cDNA having SEQ ID NO:17) can be inserted at a position between the sTF and annV sequences (with or without the linker sequences and/or purification tag sequence).

To extend the serum half-life of increase their activity, the invention also contemplates chimeric proteins containing multiple sTF domains, linked to the amino or carboxy terminus of Annexin V (such as the protein having SEQ ID NO:19 as encoded for example by a cDNA having SEQ ID NO:20).

The invention also contemplates chimeric proteins comprising sTF, or multiple sTF domains (or their derivatives as described herein) and other non-AnnV PS binding domains of proteins such as synpatotagmin I, or other proteins known to those skilled in the art, which would serve to anchor the sTF domain(s) to PS-containing membranes.

Examples of other PS-binding proteins that can be used in substitution for AnnV include, but are not limited to, Annexin family members, lactadherin, domains found in proteins known to bind PS, such as Factor V/Va, Factor X/Xa, Factor II/IIa, Factor VII/VIIa, Factor IX/IXa, Factor VIII/VIIIa, Spectrin, Class B Scavenger receptor type I, Protein Kinase C, and proteins containing the C2 domains of protein kinase C (this includes synaptotagmins), Rabphilin family members, the PS receptor, endothelial lectin-like OxLDL receptor-1 (LOX-1), antibodies to PS, phosphatidylserine decarboxylase, MARCKS (myristoylated, alanine-rich protein kinase C substrate), PS-p68, Myosin, Erythrocyte protein 4.1, hemoglobin, Calponin family members, S100A, S100B, calcyclin-binding protein family members, milk membrane-glycoprotein, MFG-E8 (milk fat globule-EGF factor 8), and other PS-binding motifs known to those of ordinary skill in the art.

In one embodiment of the invention, prior to administration of the sTF-AnnV (or any other chimeric protein contemplated herein), a subject having a tumor is first given an injection of chemotherapy which causes changes in the tumor or tumor blood vessels causing an increased binding of sTF-AnnV, for example by increasing PS expression on the surfaces of tumor or blood vessel cells. Administration of the sTF-AnnV would follow, and would bind to the tumor and tumor blood vessel in enhanced amounts. Chemotherapy is defined as any treatment that causes death of cancer cells, (i.e., drugs, chemicals, hormone, vitamins, etc.) as is well known by those of ordinary skill in the art. Another approach is to administer radiation therapy to the area (alone or with a drug therapy) in order to enhance the efficacy and/or binding of the sTF-AnnV.

Cancer cells receive signals from their environment that allow them to grow, travel, and invade normal tissues. They differ from normal cells in that many have increased numbers of certain "receptor" molecules on their surface, which help the cells survive. This invention contemplates in one embodiment new proteins designed to block tumor cell surface receptors including tissue factor and the urokinase receptor thereby altering tumor cell behavior.

In one embodiment, the invention contemplates chimeric proteins designed to inhibit signaling through cellular receptors important for cancer cells, and possibly normal inflammatory cells. In particular the invention contemplates (1) novel proteins that bind to the urokinase receptor, thereby preventing the binding of the two proteins that normally result in signaling through that receptor (urokinase and plasminogen activator inhibitor-1, also called PAI-1, and (2) novel proteins that bind to cell surfaces and contain the extracellular domain of the cell surface protein, tissue factor, which serves as a receptor for the plasma protein called Factor VIIa. Since the complex comprised of (native) tissue factor and Factor VIIa are able to generate signals that affect cancer cell behavior in a manner that is dependent upon the cytoplasmic tail of tissue factor, the chimeric proteins contemplated herein that comprise sTF will act as a sink for Factor VIIa, diverting it from the tissue factor on the surface of the cancer cell. The invention also contemplates novel proteins that bind both to the urokinase receptor and to Factor VIIa, thereby keeping cancer cells from benefiting from their own cell surface tissue factor and urokinase receptor molecules. The invention also contemplates mutants of the tissue factor domains and/or the urokinase receptor domains to increase the affinity of each of these domains for their ligands.

The urokinase receptor and tissue factor are also found on macrophages of the so-called chronic inflammatory cells. The chimeric proteins described herein can also be useful in treating human or animal diseases in which ongoing macrophage-mediated inflammation plays a role in unremitting disease or illness.

In another embodiment, the invention comprises sTF linked to ATF (sTF-ATF), a chimeric protein which blocks both the TF and urokinase receptors of the cell. ATF is the amino-terminal protein fragment of urokinase (amino acids 1-135 of the urokinase A chain, thereby denoted ATF). ATF (SEQ ID NO:22, encoded by a cDNA having SEQ ID NO:21 for example) binds to the urokinase receptor but, unlike full length urokinase, is not internalized.

The chimeric proteins of the present invention may comprise, in lieu of AnnV, one or more peptides which occupy receptors of tumor vasculature and other organs including homing peptides as described in U.S. Pat. Nos. 6,576,239; 6,491,894; 6,528,481; 6,610,651; and 6,933,281, each of which is hereby expressly incorporated herein by reference.

Other peptides that bind to the tumor vasculature and which may comprise the protein of the present invention include but are not limited to: HWGF (SEQ ID NO:23)-motif peptides (selective inhibitors of matrix metalloproteinase-2 and matrix metalloproteinase-9, also known as gelatinase A and gelatinase B), for example the synthetic peptide CTTHWGFTLC (SEQ ID NO:24) targets angiogenic blood vessels, inhibits the migration of human endothelial cells and tumor cells, and also prevents tumor growth and invasion in animal models and improves survival of mice bearing human tumors.

As noted above, any of the tumor treatment methods contemplated herein may include an initial step of performing a scan with Annexin V (not sTF-Annexin V) in order to identify subjects who would be expected to have a normal or enhanced response to treatment. A preferred subject is one who demonstrates uptake of annexin V into a tumor, without excessive uptake in non-tumorous areas. This would be a more efficacious treatment because some potential subjects might have enhanced uptake without antecedent drug and/or radiation therapy (and thus wouldn't necessarily benefit from these ancillary treatments with their attendant side effects), while others might not. The latter would be more likely to benefit by first getting chemotherapy or radiation treatment, thereby allowing for a synergistic interaction between the sTF-AnnV and the "priming" therapy.

In an annexin scan (performed before sTF-AnnV administration), Annexin V sticks to activated platelets caught up in blood clots. Therefore, an Annexin V scan might identify those subjects having an increased risk for binding sTF-AnnV and who may experience pathological thrombi in non-tumorous vascular beds (i.e., to suffer a stroke, heart attack, deep venous thrombosis, etc.). By doing an Annexin V scan first, the safety profile of the user may be improved by avoiding those at greater risk for this complication. Annexin V scans can be performed by a variety of imaging techniques (specifically magnetic resonance imaging in addition to nuclear medicine imaging), allowing for the development of new imaging compounds. Alternatively, subjects may be given an intravenous injection of annexin V, prior to administration of sTF-annV (with or without chemotherapy and/or radiotherapy), in order to prevent binding of sTF-annexin to blood vessels wherein thrombosis would be unwanted.

Experimental Procedures

Materials

Recombinant membrane-anchored TF, recombinant sTF ($TF_{2-219}$), and monoclonal antibodies to Factor VII and TF were prepared as described. A monoclonal antibody reacting with the $His_6$ tag of recombinant proteins was from Cell Signaling Technology (Beverly, Mass.). Chromozym t-PA (N-methysulfonyl-D-phenylalanylglycyl-L-arginine-4-nitroanilide acetate) and Chromozym X (N-methoxycarbonyl-D-norleucyl-glycyl-L-arginine-4-nitranilide acetate) were from Roche Diagnostics Corp (Indianapolis, Ind.). Purified human Factors X, Xa, VII, and VIIa were from Enzyme Research Laboratories (South Bend, Ind.). Unless otherwise specified, all other regents were from Sigma Chemical Co.

Phospholipids were obtained from Avanti Polar Lipid (Alabaster, Ala.) as stock solutions in chloroform and used to prepare unilamellar phospholipid vesicles. Aliquots were mixed at a molar ratio of phosphatidylcholine (PC) to PS of 4:1, and the chloroform removed by evaporation under argon. Phospholipids were resuspended in 0.1 M NaCl, 0.05 M Tris-HCl, pH 7.5, and sonicated until the suspension was almost clear, yielding PC/PS vesicles. The phospholipid concentration was determined by phosphate analysis.

Relipidation of TF into phospholipid vesicles was performed using the octyl-beta-D-glucopyranoside method, typically at TF:phospholipid molar ratios of 1:8700. The effective TF concentration was determined by titrating with increasing concentrations of Factor VIIa in solutions containing Chromozym t-PA and comparing the resulting amidolytic activity to that obtained by incubating Factor VIIa with known concentrations of sTF. The phospholipid concentration of the TF preparation was determined by phosphate analysis so that comparable amounts of PS were present when TF was compared directly to sTF-annV.

Fluorescein isothiocyanate (FITC)-annexin V was prepared by incubating FITC with Annexin V at a 2:1 molar ratio for 1 hr in the dark at room temperature in 0.5 M carbonate buffer, pH 9.5. Unbound FITC was removed by gel filtration in 150 mM NaCl, 0.01M Tris-HCl, pH 8.2, followed by dialysis against the same buffer for an additional 48 hr.

Construction of Expression Vectors

Annexin V cDNA (in the pET-22b(+) vector) was a generous gift from Dr. Antony Rosen. The sTF-annV construct was generated by ligating the cDNA encoding amino acids 2-219 of TF to the 5' end of the annexin V cDNA. The sTF cDNA was cloned by PCR using the forward primer 5'-CATGCCATGGCAGGCGCTTCAGGCACTACAAATAC-3' (SEQ ID NO:25), and the reverse primer 5'-CCCAAGTCTTGGGTTCTCTGAATTCCCCTTTCTC-3' (SEQ ID NO:26). A linker sequence encoding $(GGGGS)_3$ was inserted between the sTF and annexin V cDNA using QuikChange® Multi Site-Directed Mutagenesis Kit (Stratagene, La Jolla, Calif.) with the following primer: 5-GGGGAATTCAGAGAAGGTGGCGGTTCAGGCGGTGGAGGTTCAGGAGGTGGCGGATCAAT GGCACAGGTTCTC-3' (SEQ ID NO:27). The sTF-annV gene was cloned into the NcoI and HindIII sites of the pET-22b(+) vector. This vector codes for a protein with a $His_6$-tag at the carboxy terminus. A chimera composed of a mutated form of sTF linked to annexin V (sTFM-annV) was created by site-directed mutagenesis. Residues 164 and 165 of sTF (i.e., residues 165 and 166 of the 219 amino acid sTF) were mutated with the QuikChange® Multi Site-Directed Mutagenesis Kit (Stratagene, La Jolla, Calif.) from lysine to alanine using the primer 5'-CTTTATTATTGGAAATCTTCAAGTTCAGGAGCCGCAACAGCCAAAACAAACACTAATGAGTT TTTG-3' (SEQ ID NO:28). The sTFM-annV gene was cloned into the NcoI and HindIII sites of pET-22b(+). DNA sequencing confirmed the composition of all three constructs.

Expression and Purification of sTF-annV, sTFAA-AnnV and Annexin V.

The pET-22b(+) vectors with the sTF-annV, sTFAA-annV, or annV genes were inserted into *E. coli* strain BL-21/DE3 (Novagen, Madison, Wis.). This vector provides a signal peptide that directs the recombinant protein to the periplasmic space. Expression was induced when the $A_{600}$ of the bacterial suspension reached 0.8 by adding 0.3 mM isopropyl-beta-D-thiogalactopyranoside (IPTG) for 15 hr at 25° C. Cells were harvested, subjected to osmotic shock (5 mM $MgSO_4$), and the periplasmic fraction was collected. Recombinant proteins were purified by immobilized metal affinity chromatography using a His-Select column (Sigma, St. Louis, Mo.) equilibrated with 0.3 M NaCl, 0.05 M $NaH_2PO_4$, pH 8.0. The column was washed with the same solution in the presence of 10 and 20 mM imidazole and then eluted with 250 mM imidazole. The eluate was dialyzed against 0.1 M NaCl, 50 mM Tris-HCl pH 7.4. The purity and identity of recombinant proteins were examined by SDS-PAGE and Western blotting.

Phospholipid Binding Assay

The affinity of chimeras for phospholipid vesicles containing PS was determined by modifications of published assays using a commercially available aPTT coagulation reagent (Dade®Actin® FSL Dade Behring, Newark, Del.) as the source of PS. The reagent was reconstituted according to the manufacturer's instructions and diluted 1:10 with 140 mM NaCl, 0.01M HEPES, pH 7.5 (HBS) plus 2.5 mM $Ca^{++}$ (HBS-$Ca^{++}$). The diluted phospholipid suspension (10 mL) was incubated with 50 nM FITC-annexin V (a concentration resulting in saturation of the PS present in the assay, as determined experimentally) in HBS-$Ca^{++}$ in coated microcentrifuge tubes (Slickseal, National Scientific, Claremont, Calif.). After incubation at 37° C. for 15 min, the mixtures were centrifuged at 16,000×g for 20 min. The pellets were washed in HBS-$Ca^{++}$ and then resuspended in HBS-$Ca^{++}$ containing various amount of each of the unlabeled competing proteins (annexin V, sTF-annV or sTFAA-annV). After an additional 12 hr incubation at 37° C., the mixtures were centrifuged and the pellets washed in HBS-$Ca^{++}$. The pellets were then resuspended in HBS plus 10 mM EDTA, and incubated for 16 hr at room temperature to elute bound FITC-annexin V. The tubes were centrifuged and the supernatant fluid removed. The amount of FITC-annexin in the supernatant was determined by measuring its fluorescence (excitation wavelength, 485 nm; emission wavelength, 535 nm) in a fluorescent microplate reader (Victor2, Wallac, PerkinElmer, Boston, Mass.).

Factor VII Autoactivation Assay

The ability of the chimeric proteins to promote the autoactivation of Factor VII was assessed by adding each (final concentration, 80 nM) to Factor VII (final concentration, 80 nM) in 0.1 M NaCl, 50 mM Tris-HCl, 0.10% bovine serum albumin, pH 7.4 (TBS) with 5 mM $CaCl_2$ (TBS/$Ca^{2+}$). For experiments utilizing sTF-annV or sTF, PC/PS vesicles were added to the incubation mixtures at a composition and concentration identical to that present in the native TF preparation (total phospholipid concentration, 810 mM, PC:PS molar ratio=4:1). At selected intervals, 10 mL aliquots were removed from each incubation mixture and transferred to polystyrene tubes containing 40 mL TBS plus 5 mM EDTA to stop the reaction. The amount of Factor VIIa generated was assayed by adding 150 mL of TBS/$Ca^{2+}$, excess sTF, and Chromozym t-PA (final concentrations, 5 mM, 124 nM and 5 mM, respectively) and measuring the change in $A_{405}$.

Factor VIIa Binding Assay

The sTF/TF-induced increase in Factor VIIa amidolytic activity was used to quantify the binding of these proteins to Factor VIIa. Increasing concentrations of sTF-annV, sTFM-annV or sTF were incubated with Factor VIIa (5 nM) in TBS/$Ca^{2+}$ in 96 well assay plates. After 10 min at room temperature, Chromozym t-PA was added (1 mM final) and the initial rate of substrate hydrolysis was measured at 405 nm using a microplate reader (Molecular Devices, Menlo Park, Calif.). The background activity of Factor VIIa in the absence of sTF, sTF-annV or sTFAA-annV was subtracted from the measured values. Kinetic parameters were calculated using Prism 4 (GraphPad Software, San Diego, Calif.).

Factor X Activation

The activation of Factor X by Factor VIIa in the presence of sTF, sTF-annV, sTFAA-annV or native relipidated TF was monitored in a continuous one stage assay. sTF, sTF-annV, sTFAA-annV or native TF were added to 1 nM Factor VIIa, Factor X, PC/PS (molar ratio, 4:1) and 0.5 mM Chromozym X in TBS/$Ca^{2+}$. The rate of chromogenic substrate hydrolysis (change in $A_{405}$) was monitored over 20 min and converted to Factor Xa concentrations by reference to a standard curve prepared with purified human Factor Xa. The derivative of the resulting parabolic progress curve was taken (Softmax Pro, Molecular Devices, Menlo Park, Calif.) to determine the rate of Factor Xa generation and kinetic parameters were calculated using Prism 4 (GraphPad Software, San Diego, Calif.).

Plasma Coagulation Assays

Coagulation Times

Clotting times of normal human citrated plasma following the addition of $CaCl_2$ in the presence of various concentrations of recombinant proteins and PC/PS (molar ratio, 4:1) were measured with a mechanical coagulometer (ST-4, Diagnostica Stago, Parsipanny, N.J.), which had an upper limit of measurement of 999 s.

Dilute Activated Partial Thromboplastin Time

A commercially available aPTT reagent (Dade® Actin®, Dade Behring) was diluted 1:50 in TBS and used to measure the coagulation time of citrated human plasma in the presence of various concentrations of sTF, annexin V or sTF-annV. Plasma was incubated with dilute aPTT reagent and recombinant proteins for 3 min at 37° C., followed by the addition of 25 mM $CaCl_2$. The time required for a clot to form was measured with a mechanical coagulometer.

Activated Partial Thromboplastin Time (aPTT)

The aPTT of plasma containing either 1 unit/mL heparin sodium (American Pharmaceutical Partners, Inc. Los Angeles, Calif.) or enoxaparin sodium (Lovenox®, Aventis Pharmaceuticals, Bridgewater, N.J.) and various concentrations of sTF-annV or Factor VIIa was measured with a commercially available aPTT reagent (Actin® FSL; Dade Behring, Newark, Del.) according to the manufacturer's instructions.

Mouse Tail Bleeding Times

Mice were housed in accordance with and studied using a protocol approved by the University of Oklahoma Health Sciences Center Institutional Animal Care and Use Committee. They were injected subcutaneously with enoxaparin sodium and two hours later were anesthetized with pentobarbital (60 mg/kg, given i.p.). The tail was warmed in normal saline at 37° C., transected with a scalpel blade at a point where it was 2 mm in diameter, and then placed in a tube of normal saline maintained at 37° C. The time required for bleeding to stop was recorded. In preliminary dose-finding experiments, increasing doses of enoxaparin sodium were administered. Once a suitable dose was identified (20 mg/kg), a second bleeding time was performed 5 min after the first. The additional bleeding time was performed by transecting the tail at a point 5 mm proximal to the first. The second bleeding times were not significantly different than the first (p=0.3, two-tailed, paired t-test, Prism 4, Graphpad Software). Untested animals were then treated in a similar manner, but received an intravenous injection of sTF-annV (90 mcg/kg) immediately after the first bleeding time determination. A second bleeding time was performed 5 min after the injection. A two-tailed, paired t-test was used to compare the two bleeding times. An additional group of animals were then studied. Two hours after the SQ injection of saline or enoxaparin (20 mg/kg), mice were given IV injections of sTF-annV (90 mcg/kg), saline, sTF, annexin V or a combination of sTF and annexin V. All proteins were injected in amounts equimolar with sTF-annV. Tail bleeding times were measured 10 minutes later.

Results

Expression and Purification of Annexin V and Annexin V Chimeras cDNA constructs encoding three proteins (annexin V, sTF-annV and sTFM-annV) were expressed in the periplasmic space of *E. coli* and the proteins were purified by immobilized metal affinity chromatography (See FIG. 1 for analyses of the purified proteins by SDS-PAGE and western blotting).

sTF-annV Accelerates Plasma Coagulation

Figure 2A:
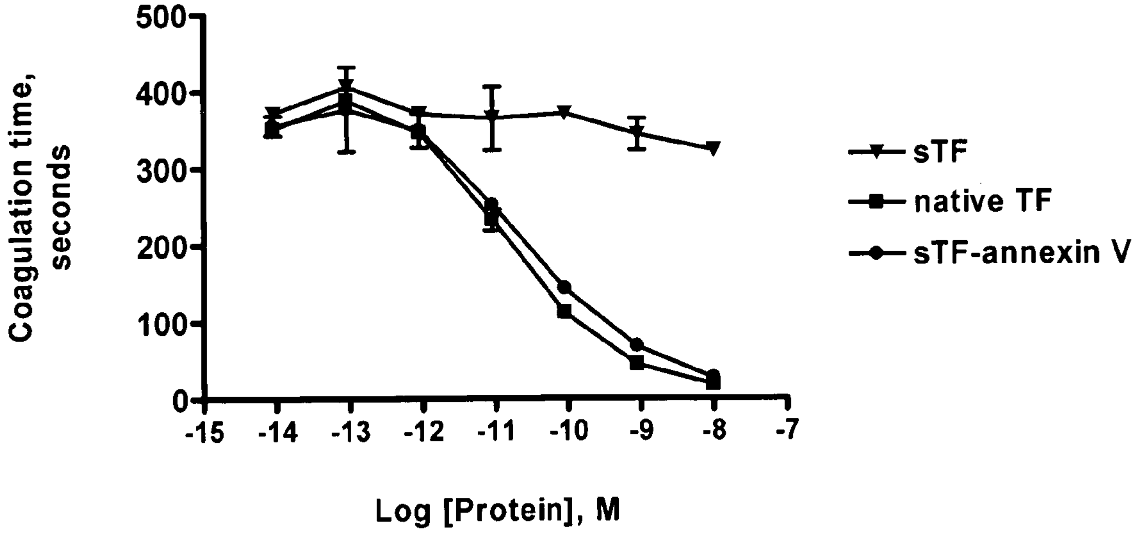
FIG. 2. Influence of recombinant proteins on plasma coagulation. A, The coagulation time of citrated human plasma with different concentrations of native TF (■), sTF (▼), or sTF-annV (●). The total amount of PC/PS added to each sample was 10 mM (PC:PS molar ratio, 4:1). Shown are means ±SEM. B, Plasma coagulation times with sTF (▼), annexin V (▲), both sTF and annexin V (♦), or sTF-annV (●) measured using a dilute partial thromboplastin time protocol, as described in Experimental Procedures. C, Plasma coagulation times, in the absence of added phospholipids, with different concentrations of sTF (▼), annexin V (▲), sTF-annV (●), or sTFAA-annV (○). Shown are means ±SEM.
Figure 2B:
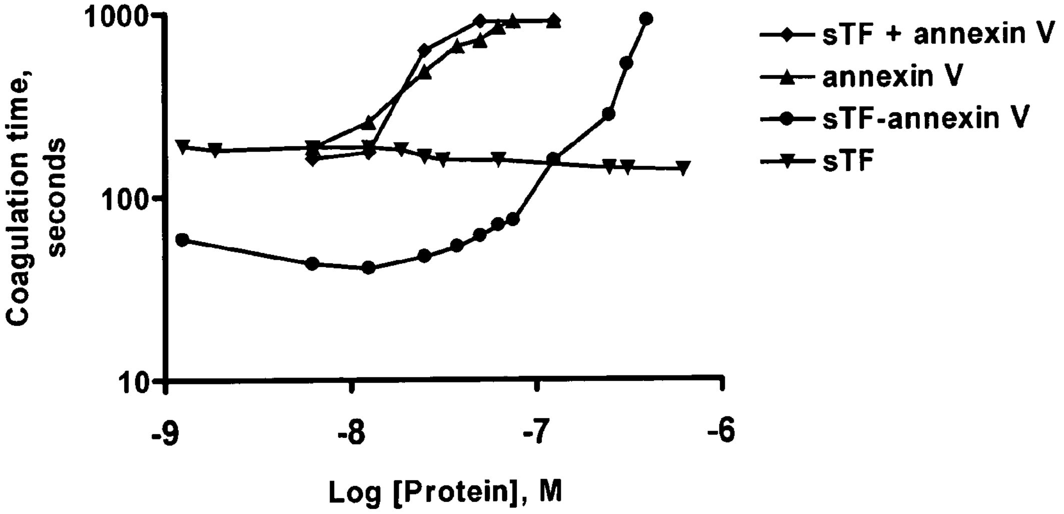

In initial studies, the abilities of sTF, native TF, and sTF-annV to accelerate plasma coagulation in the presence of identical concentrations of added phospholipid and $CaCl_2$ were compared. As shown in FIG. 2A, sTF-annV and native TF shortened the plasma coagulation time to a much greater extent than did sTF. A dilute aPTT assay was then used to determine whether the effects of sTF-annV could be duplicated by adding sTF to annexin V. Plasma was recalcified in the presence of dilute aPTT reagent (used as a source of phospholipid) and sTF, annexin V, the combination of sTF and annexin V, or sTF-annV. As shown in FIG. 2B, the simultaneous addition of sTF and annexin V did not reproduce the procoagulant effect of sTF-annV. Under these conditions, sTF-annV demonstrated a biphasic effect on plasma coagulation, prolonging coagulation at higher concentrations.

These results suggested that at lower concentrations the procoagulant effect was due to the sTF domain, while at higher concentrations the anticoagulant effect of annexin V predominated. To test this hypothesis, a construct was prepared in which the lysines at positions 165 and 166 of the TF/sTF domain (164 and 165 of the 218 aa sTF) were mutated to alanine, a change known to impair Factor X activation. The resulting chimera (sTFAA-annV) also exhibited biphasic effects on plasma coagulation (FIG. 2C), but had less procoagulant activity than sTF-annV and exhibited its anticoagulant activity at lower concentrations. Given the evidence that sTF-annV and sTFAA-annV were able to alter plasma coagulation, detailed functional characterization of their constituent domains was undertaken.

Phospholipid Binding Activity

Figure 3:
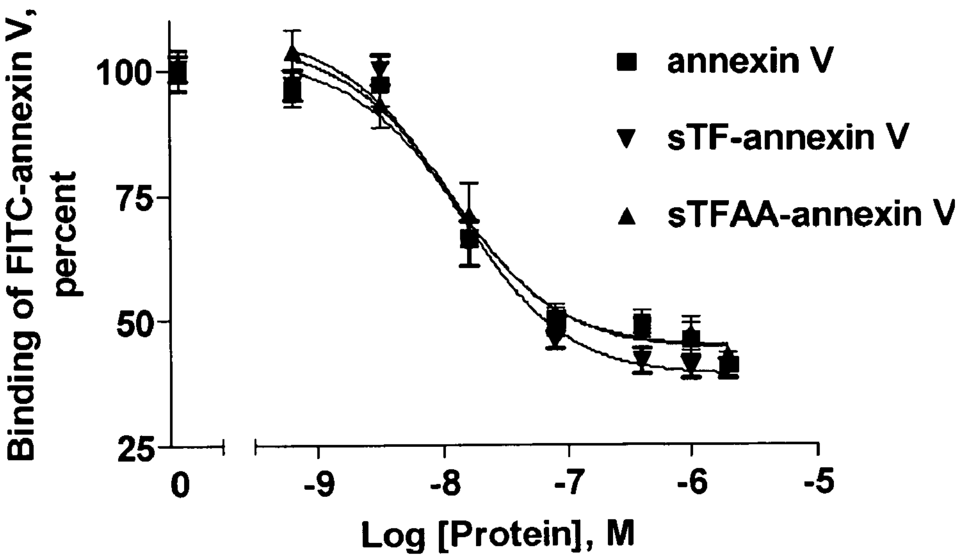
FIG. 3. Phospholipid binding of sTF-annV, and sTFAA-annV. The ability of sTF-annV (●) and sTFAA-annV (○) to bind PC/PS vesicles was compared to that of annexin V (▲) by assessing the ability of each protein to displace FITC-annexin V from a phospholipid suspension, as described in Experimental Procedures. The curves were computer using non-linear regression and a one site ligand binding equation. Data are expressed as the percent (mean ±SEM) of EDTA-elutable fluorescence.

The ability of sTF-annV and sTFAA-annV to bind PS was assessed with a modification of a published PS-binding assay in which annexin V, sTF-annV or sTFAA-annV competed with FITC-annexin V for binding to phospholipid vesicles. As shown in FIG. 3, both chimeras exhibited PS-binding activity comparable to annexin V. The $K_d$ for annexin V was 12 nM; for sTF-annV, 13 nM, and sTFAA-annV, 11 nM.

Factor VII Autoactivation Activity

Figure 4:
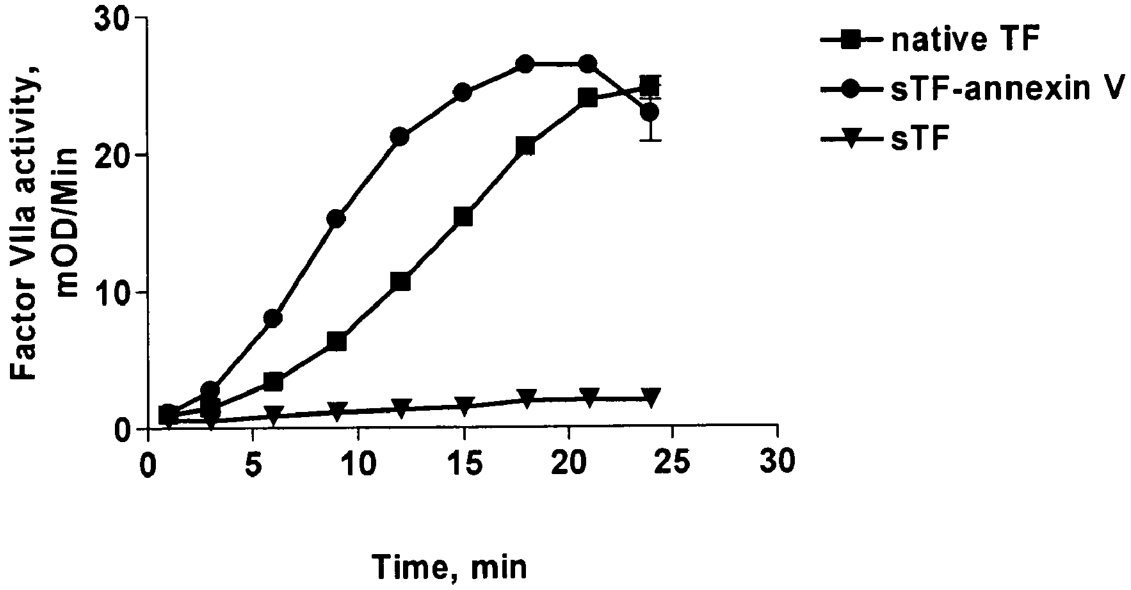
FIG. 4. Autoactivation of Factor VIIa in the presence of native TF, sTF-annV or sTF. Factor VII (80 nM) was added to equimolar concentrations of native TF (■), sTF (▼), or sTF-annV (●) in the presence of PC/PS (810 mM, PC:PS molar ratio=4:1) and $CaCl_2$. At the indicated times, aliquots were removed and the reaction stopped by dilution in EDTA-containing solutions. The Factor VIIa content of each sample was then determined by measuring the rate of hydrolysis of Chromozym t-PA in the presence of added sTF and $CaCl_2$. Shown are means ±SEM.

It has been shown previously that TF, but not sTF, promotes autoactivation of Factor VII in the presence of PS and $Ca^{2+}$. The failure of sTF to accelerate Factor VII autoactivation has been attributed to the low affinity of sTF:VIIa complexes for PS-containing membranes. Since the annexin V domain of the chimera exhibited high affinity for PS-containing liposomes, we postulated that sTF-annV would promote Factor VII autoactivation in a manner comparable to TF, rather than sTF. As shown in FIG. 4, sTF-annV promoted Factor VII autoactivation at a rate comparable to native TF, rather than sTF (which was inactive). These results also suggest that sTF-annV is able to bind Factor VII as well as native TF.

Factor VIIa Binding Activity

To measure the binding of Factor VIIa to the chimeras, we quantified the increase in Factor VIIa's amidolytic activity when its binds to TF/sTF. Because sTF does not bind membranes well, we performed the analysis in the absence of PS. Both sTF-annV and sTFM-annV increased the amidolytic activity of Factor VIIa to the same extent as sTF, indicating that the annexin V domain did not interfere with the ability of the sTF domain to bind Factor VIIa (data not shown). The $K_d$ for binding of Factor VIIa to sTF was 8.17 nM; for sTF-annV, 7.05 nM; and for sTFAA-annV, 3.47 nM, all in the absence of phospholipid vesicles.

Factor X Activation

Figure 5A:
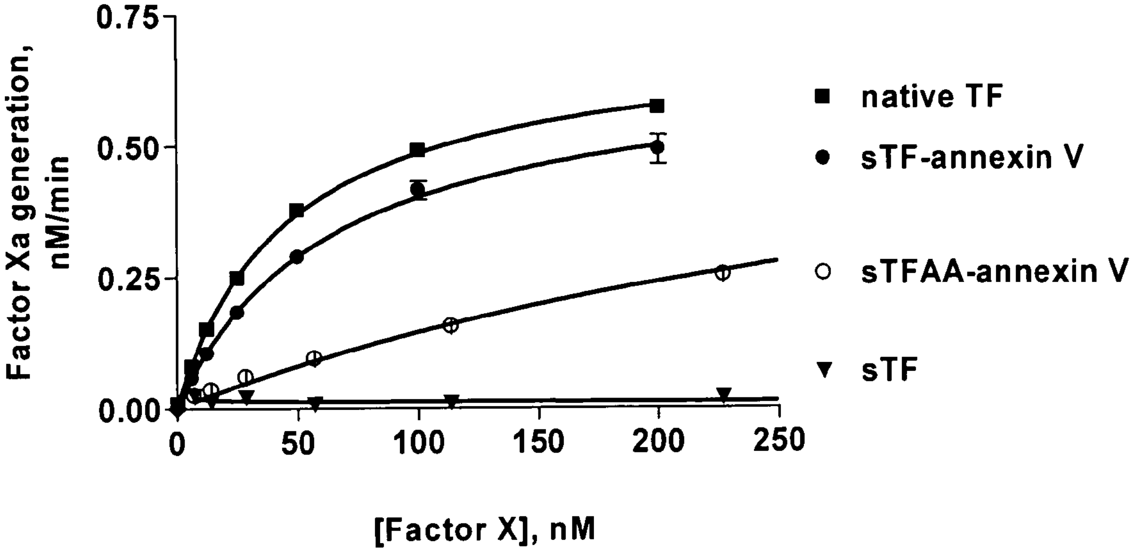
FIG. 5. Generation of Factor Xa by Factor VIIa in the presence of recombinant proteins. A, Various concentrations of Factor X were added to 1 nM Factor VIIa, 5 mM PC/PS (molar ratio, 4:1), 5 mM $CaCl_2$ and Chromozym X substrate in the presence of 5 μM native TF (■), sTF (▼), sTF-annV (●), or sTFAA-annV (○). Initial rates of substrate hydrolysis were measured as described in Experimental Procedures, to which the Michaelis-Menten equation was fit. B, Initial rates of Factor Xa generation were measured in solutions containing 28 nM Factor X, 5 mM $CaCl_2$ 1 nM Factor VIIa, 0.347 mM PC/PS and various concentrations of sTF (▼) or sTF-annV (●).

The effect of sTF-annV and sTFM-annV on the rate of Factor X activation by Factor VIIa was assessed. As shown in FIG. 5A, the rate of Factor X activation in the presence of either sTF-annV or sTFM-annV was greater than that seen in the presence of sTF. As expected from prior studies of sTFM, sTF-annV was more potent than sTFAA-annV in supporting Factor X activation. As shown in Table 1, the catalytic efficiency ($k_{cat}/K_m$) of Factor VIIa in the presence of sTF-annV was approximately 67% of that found in the presence of native TF, but approximately 5-fold greater than that of sTFAA-annV.

Figure 5B:
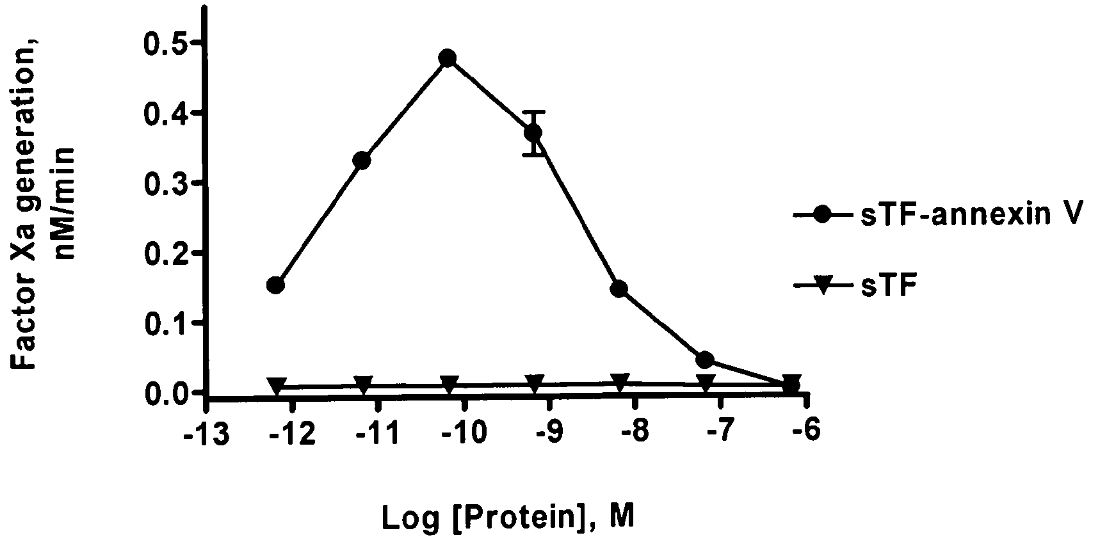

Since high concentrations of sTF-annV were associated with prolongation of the plasma coagulation times, we studied the effect of increasing concentrations of sTF-annV on the rate of Factor X activation by Factor VIIa. As shown in FIG. 5B, sTF-annV exhibited a biphasic effect on Factor X activation, paralleling its effects on plasma coagulation.

TABLE 1

| Cofactor | $V_{max}$ nM · min$^{-1}$ | $k_m$ nM | $k_{cat}$ s$^{-1}$ | $k_{cat}/k_m$ μM$^{-1}$s$^{-1}$ |
|---|---|---|---|---|
| TF | 0.71 ± 0.008 | 46 ± 1 | 2.37 | 51.5 |
| sTF-annV | 0.66 ± 0.03 | 64 ± 7 | 2.2 | 34.4 |
| sTFAA-annV | 0.71 ± 0.06 | 389 ± 58 | 2.37 | 6.1 |

Figure 6A:
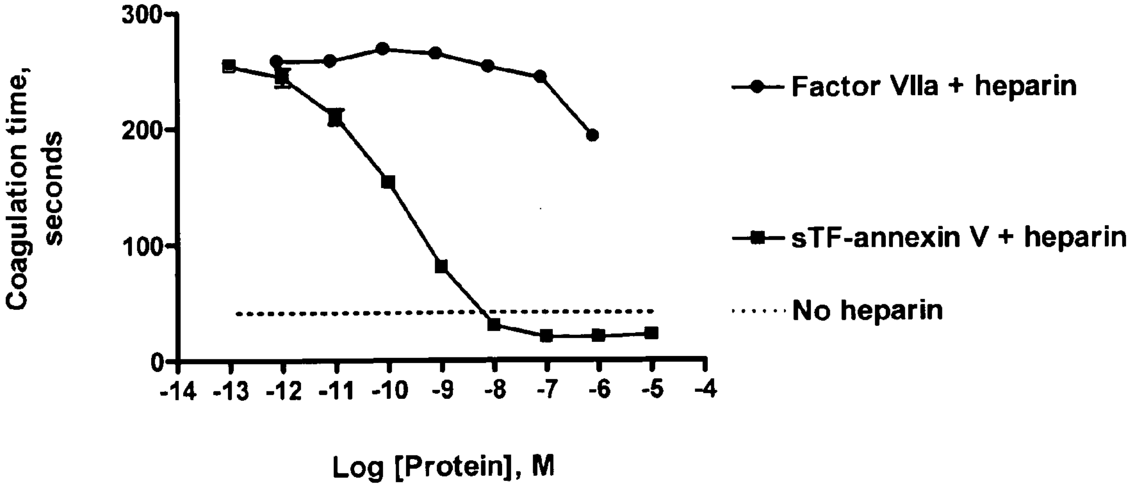
FIG. 6. The effect of sTF-annV or Factor VIIa on the aPTT of heparin-treated plasma. A, aPTT assays of plasma containing heparin sodium (1 unit/mL) was measured in the presence of various concentrations of Factor VIIa (●) or sTF-annV (■). B, The aPTT of plasma containing enoxaparin sodium (1 unit/mL) was measured in the presence of various concentrations of Factor VIIa (●) or sTF-annV (■). The dotted lines show the mean clotting time for the aPTT assay in the absence of heparin or enoxaparin. Shown are means ±SEM. (Most error bars are too small to be seen.)
Figure 6B:
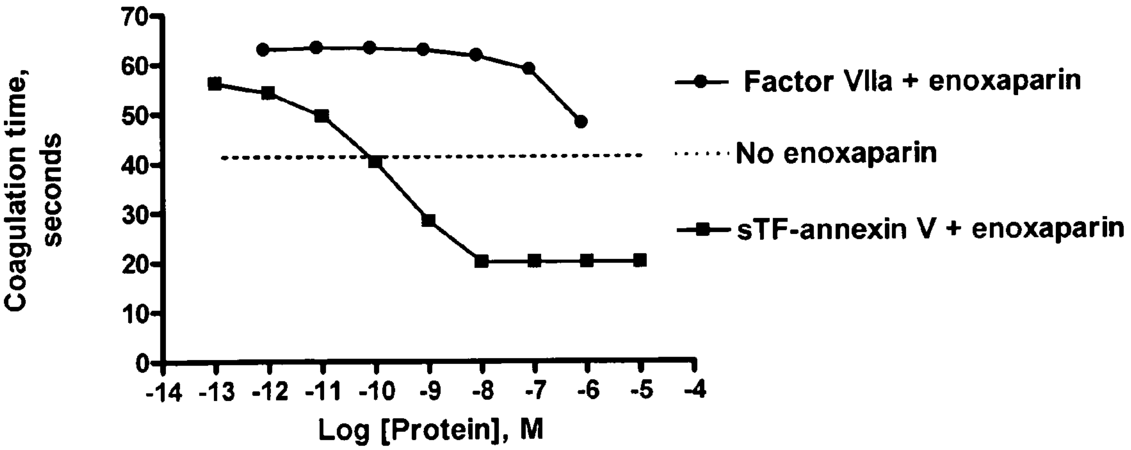

Effect of sTF, sTF-annexin V, and sTFAA-annV on the Rate of Factor X Activation by Factor VIIa Effect of sTF-annexin on Coagulation in the Presence of Heparin Heparin is a commonly used anticoagulant that works by enhancing the ability of the serpin, antithrombin, to inhibit (primarily) Factor Xa and thrombin. We added unfractionated heparin sodium or enoxaparin, a low molecular weight heparin, to citrated plasma along with various concentrations of sTF-annV and then determined the plasma aPTT. sTF-annV shortened the aPTT of plasma containing either 1 unit/mL unfractionated heparin (FIG. 6A) or 1 unit/mL enoxaparin (FIG. 6B). Factor VIIa, used as a therapeutic agent to treat bleeding in numerous clinical conditions associated with decreased thrombin generation, also decreased the aPTT of heparin-treated plasma, although less potently than sTF-annV (FIGS. 6A and 6B).

Effect of sTF-annV on Mouse Tail Bleeding Times

Figure 7A:
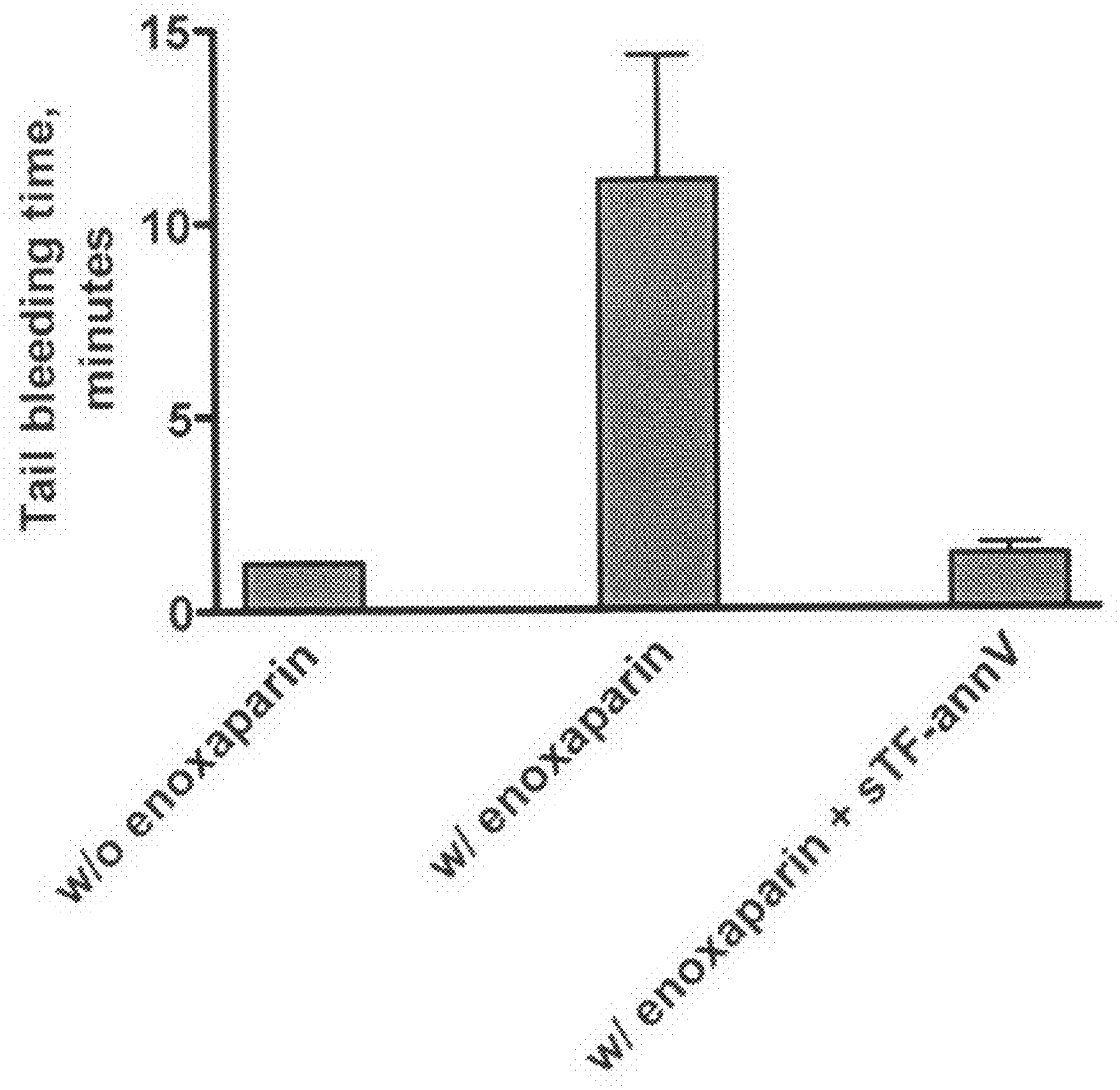
FIG. 7. The effect of sTF-annV on the tail bleeding time. Panel A: Mice (n=13) were given a subcutaneous injection of enoxaparin sodium (20 mg/kg), and two h later they were anesthetized and the tail bleeding time determined as described in the Experimental Procedures. Immediately upon the cessation of bleeding, the animals were injected intravenously with sTF-annV (90 mcg/kg) in TBS. Five min later the bleeding time was measured again. The differences were significant at a level of p=0.01 (paired two-tailed t-test). Panel B: Tail bleeding times were measured as described above. 2 hours after receiving SQ enoxaparin (or saline) animals were injected intravenously with sTF-annV (90 mcg/kg) or equivalent molar amounts of sTF, annexin V or both sTF and annexin V. Tail bleeding times were measured 10 min later. sTF-annV shortened the bleeding time of mice that did not receive enoxaparin ($p>0.2$) as well as those that did ($p<0.0001$, two-tailed unpaired t-test with Welch's correction). Two animals were studied in each of the groups that did not receive enoxaparin, and 4 in each of the enoxaparin-treated groups.

Although the template bleeding time assay in humans is thought to predominantly reflect platelet function, defects in thrombin generation in mice are reflected by prolonged bleeding times. We therefore administered enoxaparin to normal mice to determine whether sTF-annV would affect an in vivo measure of thrombin generation. Mice were injected subcutaneously with enoxaparin sodium (20 mg/kg), a drug known to inhibit thrombin generation and the bleeding time measured 2 hours later. After the bleeding from the bleeding time wound stopped, the animals were given an intravenous injection of sTF-annV (90 mcg/kg) and the bleeding time repeated 5 min later. (Preliminary experiments showed that a second bleeding time in enoxaparin-treated animals was not significantly different than the first, p=0.3, paired two-tailed t-test.) As shown in FIG. 7A, sTF-annV significantly shortened the bleeding time of enoxaparin-treated mice (p=0.01, paired two-tailed t-test). Enoxaparin treatment resulted in a mean bleeding time of 10.7 minutes (median, 6.1 minutes). The mean bleeding time after sTF-annV treatment was 1.4 minutes (mean, 1.1 minutes). The mean bleeding time of untreated animals was 1.2 minutes.

Figure 7B:
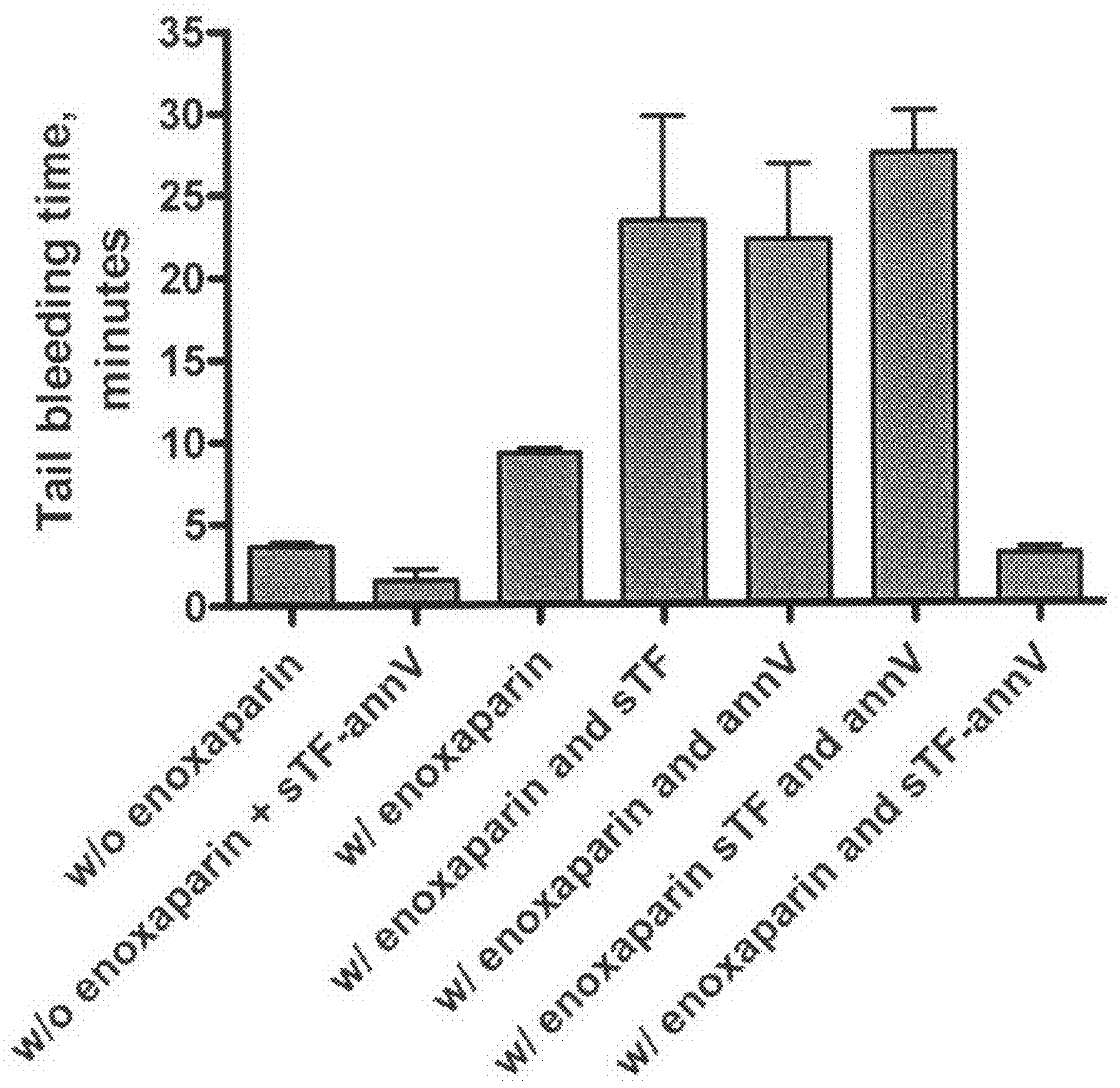

The tail bleeding time was measured in additional groups of mice. sTF-annV shortened the bleeding time of animals not treated with enoxaparin (1.5±0.7 min versus 3.6±0.2 min, $p>0.02$, unpaired t-test with Welch's correction; FIG. 7B). Naïve animals were then treated with enoxaparin (20 mg/kg, SQ) 2 h before they were injected IV with sTF-annV (90 mcg/kg) or equimolar amounts of sTF, annexin V, or the combination of sTF and annexin V. As shown in FIG. 7B, shortening of the bleeding time was only seen in animals treated with sTF-annV ($p<0.0001$, two-tailed unpaired t-test with Welch's correction), showing that the chimera itself, and not its individual constituents, was responsible for the shortening of the bleeding time.

Previous studies have shown that the isolated extracellular domain of TF (sTF) retains a conformation sufficient to allow binding to Factor VIIa, and enhancement of its cleavage of a small tripeptidyl synthetic substrate. sTF is much less efficient in promoting the activation of Factor X by Factor VIIa, however. This appears to be due to relatively low affinity of sTF and the sTF-VIIa complex for membrane surfaces. By substituting a glycosylphosphatidylinositol anchor for the TF transmembrane domain, Paborsky et al. were able to create a membrane-bound sTF variant that had full procoagulant activity, indicating the ability of sTF to function as well as native TF if appropriately tethered to a cell surface.

Others have coupled sTF to peptide moieties and demonstrated activation of the coagulation system in vitro and in vivo. Each utilized a targeting domain specific for a particular cell type or anatomic region and all of these studies were directed towards developing anti-cancer agents, rather than novel hemostatic compounds.

In the present work, a chimeric protein containing the sTF domain has been created in a preferred embodiment to have several novel features: (1) it is "poly-specific" with regard to the cell types that play a role in hemostasis; and (2) it has a membrane-targeting domain that has anticoagulant properties. Thus, although annexin V's potency as a PS-binding protein makes it attractive as a targeting moiety, its anticoagulant action cautions against its use in a construct designed to be a procoagulant hemostatic agent.

Figure 2C:
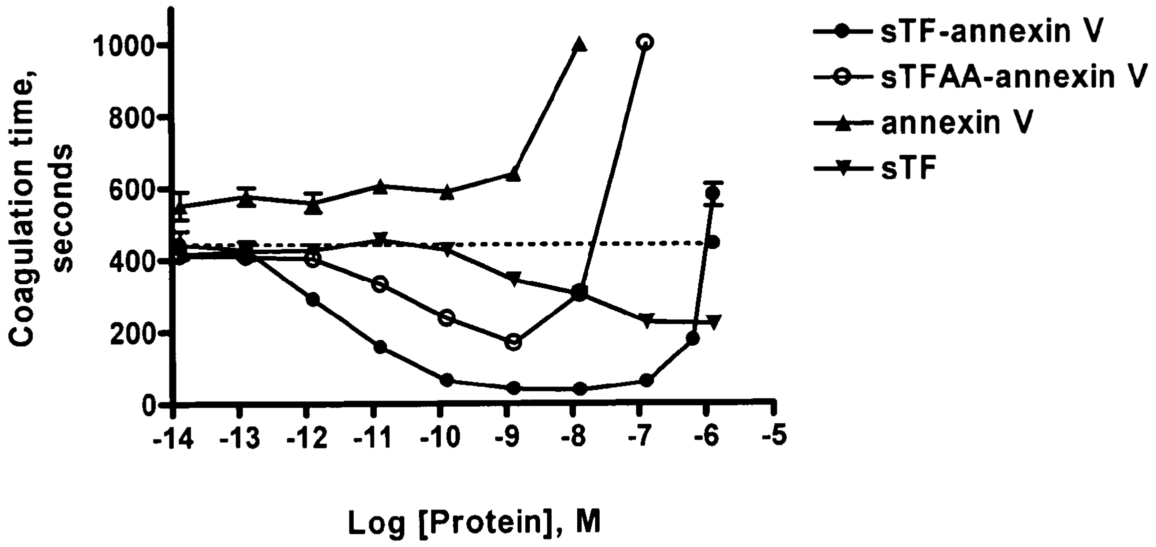

The initial studies of sTF-annV were therefore directed towards determining whether it was in fact procoagulant, and if so, how its procoagulant activity compared to that of both sTF and native TF. Because we recognized that the ratio of annexin V to phospholipid could be important, we utilized phospholipid suspensions, rather than activated cells, to maintain consistency, during our analysis. Once we found that sTF-annV was procoagulant (FIG. 2A), we established that the procoagulant activity was specific to the chimera, and could not be reproduced by adding equimolar amounts of a mixture of independent sTF and annexin V (FIG. 2B). We also prepared a chimera (referred to herein as sTFAA-annV) in which amino acids 165 and 166 of sTF were mutated from lysine to alanine, a change known to significantly reduce the procoagulant activity of TF and found that it had diminished procoagulant activity (FIG. 2C). Finally, we explored the consequences of altering the ratio of the chimera to the PS present in the reaction mixture. We found that for both sTF-annV and sTFAA-annV, an increase in the protein:PS ratio beyond a certain point resulted in an anticoagulant effect (FIG. 2C). Thus, targeting of sTF to a membrane surface by the annexin V domain is procoagulant when there is a functional excess of PS-bearing sites that can bind other coagulation factors. As the amount of annexin V present increases, those sites become less accessible to coagulation Factors VII/VIIa, X, VIII, IX, V and II, and coagulation slows.

We then conducted analyses of the functional domains comprising sTF-annV, to determine if linking them together caused a loss or gain of function of either. Tests of the chimera's ability to bind PS-containing vesicles (FIG. 3), promote Factor VII autoactivation (FIG. 4), enhance Factor VIIa's amidolytic and Factor X-cleaving activity (FIG. 5) indicated that both the sTF and annexin V domains were functional, although native TF promoted the catalytic efficiency of Factor VIIa towards Factor X twice as well as did sTF-annV (see Table 1).

These studies indicated that sTF-annV could function as a procoagulant, but its procoagulant activity was heavily dependent upon the phospholipid concentration. Since the local concentration of PS at a wound site in vivo is not precisely known, in vitro experiments have limited ability to predict the behavior of a PS binding protein (such as sTF-annV) in vivo. In order to test sTF-annV in vivo under conditions where the PS concentration would be determined by the body's response to injury, we performed tail bleeding times in mice, a method known to be sensitive to defective thrombin generation in the setting of the prior administration of enoxaparin, a low molecular weight heparin, used to impair thrombin generation. In preparation for this experiment, we studied the effect of sTF-annV on plasma coagulation in the presence of enoxaparin, as well as unfractionated heparin, and contrasted it with the effects of Factor VIIa, a protein currently used to treat patients with a variety of bleeding disorders. Both Factor VIIa and sTF-annV shortened the coagulation time of heparin- and enoxaparin-treated plasma, although sTF-annV was several orders of magnitude more potent than Factor VIIa (FIG. 6).

We treated mice with increasing doses of enoxaparin, establishing a dose that increased two sequential bleeding times reproducibly. We then injected sTF-annV by intravenous tail vein injection between the first and second tail bleeding time. In all animals tested, the second bleeding time was significantly shorter than the first. Using additional animals, we found that the effect of sTF-annV could not be reproduced by independently injecting sTF, annexin V or a mixture of the two. Because human Factor VIIa is not fully active in mouse plasma, it could not be used for direct comparisons. The dose of sTF-annV was chosen because it is equivalent (on a weight basis) to a commonly recommended recombinant Factor VIIa dose.

These studies demonstrate that seemingly antagonistic protein domains may be combined in a chimeric molecule to generate a protein whose activity is not simply determined by the net effect of its dominant domain. The protein sTF-annV exhibits an effect that is reflective of either of its opposing domains, depending upon the conditions. The ability of sTF-annV to exhibit both procoagulant and anticoagulant activity makes it a unique among hemostatic molecules.

Because AnnV binds to PS, and PS is required for blood coagulation, AnnV when used alone prevents proteins of the clotting mechanism from binding to PS thus AnnV actually inhibits blood coagulation and thus generally would not be considered to be a hemostatic agent. Even though sTF, in high concentrations can accelerate blood coagulation, a complex of sTF and AnnV, as described in this invention, would not be an obvious method of improving blood coagulation, and might well be expected by those knowledgeable in the art to either have no hemostatic effect or to have an anticoagulant effect due to the presence of the AnnV domain.

The current invention has proven to be more effective than sTF alone, at low concentrations. Without wishing to be constrained by theory, this may be due to the fact that the AnnV domain brings sTF close to the membrane surface, where Factor X is bound.

Plasma-derived hemostatic agents have been shown to induce thrombosis (unwanted blood coagulation) in some patients and thrombosis has also been seen in some trauma patients treated with recombinant Factor VIIa.

The present invention has a means (the AnnV domain or other domains described herein) of localizing sTF to areas of activated platelets, which is likely to provide a greater measure of safety, as compared to comparably effective hemostatic compounds which circulate throughout the vasculature.

Our work has shown that at higher concentrations, the sTF-AnnV protein loses its procoagulant (hemostatic) effectiveness, and becomes an anticoagulant, as evidenced by a prolongation of the blood clotting time. This is likely due to the fact that at high concentrations, the effect of the AnnV domain becomes more important than its effect of localizing the sTF domain to the membrane surface due to occupation of potential binding sites for Factor X. No other hemostatic agent is reported to have the property of being anti-coagulant at high concentrations. This feature is likely to make sTF-AnnV a safer hemostatic agent than others currently available.

Utility

The chimeric proteins of the present invention can be used in a variety of therapeutic applications related to hemostasis and thrombosis.

Use as a Hemostatic Agent.

The present invention contemplates the administration of the chimeric protein sTF-AnnV (or sTF chimera linked to other PS binding elements as described herein) to bleeding patients with the intent of increasing the generation of thrombin in the bleeding area, leading to a cessation of bleeding. Often, applying pressure or a suture will cause bleeding to stop. However, there are some circumstances when this cannot be easily accomplished wherein a compound such as sTF-AnnV would be useful. Such situations include (1) bleeding in the presence of an anticoagulant drug, (2) bleeding due to the lack (congenital or non-congenital) of one or more coagulation factors such as may be seen in trauma and massive transfusion, vitamin K deficiency, hemophilia, development of antibodies to blood coagulation factors, (3) liver disease, (4) bleeding in situations where pressure to the bleeding area is ineffective or cannot be applied, such as bleeding from diffuse areas of injury, bleeding from esophageal varices, gastritis, cystitis, endometritis, vascular injury or head trauma, (5) bleeding in situations where platelets are not present in adequate number, (6) bleeding in situations where platelets are not functioning properly, or (7) as an adjunct to use of recombinant Factor VIIa (an FDA-approved drug) in the treatment of patients with bleeding disorders.

Use in Inducing Thrombosis

Also envisioned is the use of sTF-annV or similar chimeric proteins described herein to induce thrombosis in blood vessels not related to a cancerous state, but which are potentially deleterious to the host. Such collections of blood vessels include, but are not limited to, telangiectasias, arterial malformations, venous malformations, capillary malformations, lymphatic malformations, arterio-venous malformations, hemangiomas, or aneurysms. In addition, the invention envisions using the described proteins to treat areas characterized by the growth of structurally normal blood vessels in a manner or site that may compromise the well being of the host, sometimes collectively referred to as areas of “neovascularization”. It is envisioned that sTF-annV or variations thereof would be administered to the host (by any of the variety of routes described herein) in order to induce localized thrombosis in a therapeutic manner. It may be necessary to utilize another treatment modality before, or simultaneously, in order to improve the efficacy of sTF-annV. Such adjunctive treatments might include drugs, chemicals, electrical stimulation, or radiation therapy.

Use in Cancer Treatment.

Annexin V binds to tumors and/or blood vessel cells within a tumor. Localization of sTF to tumors via annexin V (or other PS binding structure described herein) will lead to the initiation of blood coagulation within the tumor, thereby cutting off the flow of nutrients carried into the tumor, and leading to death of the tumor. The present invention utilizes the AnnV domain or of the PS binding structures to localize the chimeric protein to the tumor.

Use in Targeting Therapeutic Moieties.

The invention also contemplates the use of sTF-annV to deliver therapeutic materials, such as radioactive materials or chemotherapeutic compounds to tumors or abnormal vascular beds. In one embodiment for example, the therapeutically augmented (for example, radioactive) sTF-annV is injected into a cancer-bearing host. Localization of the therapeutically active sTF-annexinV into the tumor vessels, perhaps following the administration of chemotherapy, radiotherapy, or other manipulations designed to increase the targeting of the sTF-annV to the desired region, will augment the therapeutic effect of the molecule. The use of such modified sTF-annV molecules linked to a radioactive or chemotherapeutic moiety will be of use in treating any of a variety of cancers, vascular tumors, or vascular malformations. Examples of how chemotherapeutic or radioactive materials can be linked to proteins are shown in U.S. Pat. Nos. 6,074,643; 6,696,478; 6,403,771; 5,620,675; 5,346,686; 5,219,556; 6,852,318, 5,863,538; 7,001,991; 5,108,987; 5,000,935; 4,895,714; and 4,886,780, each of which is hereby expressly incorporated herein by reference.

A “therapeutically effective amount” or “biologically-effective amount” of a compound of the present invention refers to an amount which is effective in controlling, inhibiting, reducing, or promoting hemostasis or thrombosis or controlling, inhibiting, or reducing tumor growth. The term “controlling” is intended to refer to all processes wherein there may be a slowing, interrupting, arresting, or stopping of the progression of the disease or condition and does not necessarily indicate a total elimination of all disease symptoms.

The term “therapeutically effective amount” or “biologically effective amount” is further meant to define an amount resulting in the improvement of any parameters or clinical symptoms characteristic of the disease condition. The actual dose will be different for the various specific molecules, and will vary with the patient’s overall condition, the seriousness of the symptoms, and counter indications.

As used herein, the term “subject” or “patient” refers to a warm blooded animal such as a mammal which is afflicted with a particular disease state and needing the therapy as described herein. It is understood that guinea pigs, dogs, cats, rats, mice, horses, cattle, sheep, 200 animals, livestock, and humans are examples of animals within the scope of the meaning of the term.

A therapeutically effective amount or biologically-effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease or condition involved; the degree of or involvement or the severity of the disease or condition; the response of the individual subject; the particular compound administered; the mode of administration; the bioavailability characteristic of the preparation administered; the dose regimen selected; the use of concomitant medication; and other relevant circumstances.

A therapeutically effective amount or biologically effective amount of a compound of the present invention also refers to an amount of the compound which is effective in treating the disease condition or another condition described herein.

A therapeutically effective amount or biologically effective amount of the compositions of the present invention will generally contain sufficient active ingredient (i.e., the chimeric protein) to deliver from about 0.1 ng/kg to about 100 mg/kg (weight of active ingredient/body weight of patient). Preferably, the composition will deliver at least 10 ng/kg to 50 mg/kg, and more preferably at least 100 ng/kg to 10 mg/kg.

Practice of the method of the present invention comprises administering to a subject a therapeutically effective amount or biologically effective amount of the active ingredient, in any suitable systemic or local formulation, in an amount effective to deliver the dosages listed above. The dosage can be administered on a one-time basis, or (for example) from one to five times per day or once or twice per week, or continuously via a venous drip, depending on the desired therapeutic effect.

As noted, preferred amounts and modes of administration are able to be determined by one skilled in the art. One skilled in the art of preparing formulations can readily select the proper form and mode of administration depending upon the particular characteristics of the compound selected, the disease state or condition to be treated, the stage of the disease or condition, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally or parenterally (i.e., subcutaneously, intravenously, intramuscularly, intraperitoneally, or intratracheally), intraocularly, or intracranially.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. The dosages may be enterically coated.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically under certain conditions. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000, but are not limited to ratios within this range. Preparation of compositions for local use are detailed in *Remington's Pharmaceutical Sciences*, latest edition, (Mack Publishing).

Additional pharmaceutical methods may be employed to control the duration of action. Increased half-life and controlled release preparations may be achieved through the use of polymers to conjugate, complex with, or absorb the protein described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, and the appropriate concentration of macromolecules as well as the methods of incorporation, in order to control release.

Another possible method useful in controlling the duration of action by controlled release preparations and half-life is incorporation of the chimeric protein or its functional derivatives into particles of a polymeric material such as polyesters, polyamides, polyamino acids, hydrogels, poly(lactic acid), ethylene vinylacetate copolymers, copolymer micelles of, for example, PEG and poly(1-aspartamide).

The half-life of the proteins described herein can be extended by their being conjugated to other molecules such as polymers using methods known in the art to form drug-polymer conjugates. For example, the proteins can be bound to molecules of inert polymers known in the art, such as a molecule of polyethylene glycol (PEG) in a method known as "pegylation". Pegylation can therefore extend the in vivo lifetime and thus therapeutic effectiveness of the protein molecule. Pegylation also reduces the potential antigenicity of the protein molecule. Pegylation can also enhance the solubility of the proteins thereby improving their therapeutic effect. PEGs used may be linear or branched-chain.

PEG molecules can be modified by functional groups, for example as shown in Harris et al., (9) the entirety of which is hereby expressly incorporated herein by reference, and the amino terminal end of the protein, or cysteine residue if present, or other linking amino acid therein can be linked thereto, wherein the PEG molecule can carry one or a plurality of one or more types of the proteins or, the protein can carry more than one PEG molecule.

By "pegylated ptotein" is meant a protein of the present invention having a polyethylene glycol (PEG) moiety covalently bound to an amino acid residue or linking group of the protein.

By "polyethylene glycol" or "PEG" is meant a polyalkylene glycol compound or a derivative thereof, with or without coupling agents or derivatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides.

The PEG can be linked to any N-terminal amino acid of the protein, and/or can be linked to an amino acid residue downstream of the N-terminal amino acid, such as lysine, histidine, tryptophan, aspartic acid, glutamic acid, and cysteine, for example or other such amino acids known to those of skill in the art. Cysteine-pegylated proteins, for example, are created by attaching polyethylene glycol to a thio group on a cysteine residue of the protein.

The chemically modified chimeric proteins contain at least one PEG moiety, preferably at least two PEG moieties, up to a maximum number of PEG moieties bound to the protein without abolishing activity, e.g., the PEG moiety(ies) are bound to an amino acid residue preferably at or near the N-terminal portion of the protein.

The PEG moiety attached to the protein may range in molecular weight from about 200 to 20,000 MW. Preferably the PEG moiety will be from about 1,000 to 8,000 MW, more preferably from about 3,250 to 5,000 MW, most preferably about 5,000 MW.

The actual number of PEG molecules covalently bound per chemically modified protein of the invention may vary widely depending upon the desired protein stability (i.e. serum half-life).

Proteins contemplated herein can be linked to PEG molecules using techniques shown, for example (but not limited to), in U.S. Pat. Nos. 4,179,337; 5,382,657; 5,972,885; 6,177,087; 6,165,509; 5,766,897; and 6,217,869; the specifications and drawings each of which are hereby expressly incorporated herein by reference. Alternatively, the serum half-life of the chimeric protein can be extended by lengthening the chimeric proteins with additional amino acids or polypeptides, for example by having several sTF domains in a series, or by attaching a suitable protein which is compatible with the subject being treated, such as human serum albumin in human subjects.

Alternatively, it is possible to entrap the chimeric proteins in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences*.

U.S. Pat. No. 4,789,734 describe methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis (10). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the compounds of the invention may be incorporated into pharmaceutical preparations which may be used for therapeutic purposes. However, the term "pharmaceutical preparation" is intended in a broader sense herein to include preparations containing a chimeric protein composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of a chimeric protein, i.e., that amount necessary for preventative or curative health measures. If the pharmaceutical preparation is to be employed as a reagent or diagnostic, then it should contain reagent or diagnostic amounts of a chimeric protein.

The present invention is not to be limited in scope by the specific embodiments described herein, since such embodiments are intended as but single illustrations of one aspect of the invention and any functionally equivalent embodiments are within the scope of this invention. Indeed, various modifications of the compounds and methods of the invention in addition to those shown and described herein will become apparent to those skilled in the art from the foregoing description.

Each of the references, patents or publications cited herein is expressly incorporated herein by reference in its entirety.

REFERENCES

1. Xu et al. Endothelial and macrophage upregulation of urokinase receptor expression in human renal cell carcinoma, Human Pathology, 28, 206-213, 1997.

2. Ruoslahti E. Vascular zip codes in angiogenesis and metastasis, Biochemical Society Transactions, 32, 397-402, 2004.

3. Koivunen et al., Tumor targeting with a selective gelatinase inhibitor, Nature Biotechnology, 17, 768-774, 1999

4. Osterud B. Tissue factor: a complex biological role. Thromb Haemost 1997; 78(1):755-8.

5. Ruf W, Rehemtulla A, Morrissey J H, Edgington T S. Phospholipid-independent and -dependent interactions required for tissue factor receptor and cofactor function. J Biol Chem 1991; 266(4):2158-66.

6. van Heerde W L, de Groot P G, Reutelingsperger C P. The complexity of the phospholipid binding protein Annexin V. Thromb Haemost 1995; 73(2): 172-9.

7. Tait J F. Gibson D. Phospholipid binding of annexin V: effects of calcium and membrane phosphatidylserine content. Arch Biochem Biophys 1992; 298(1):187-91.

8. Reutelingsperger C P. Annexins: key regulators of haemostasis, thrombosis, and apoptosis. Thromb Haemost 2001; 86(1):413-9.

9. Harris et al., Pegylation, A Novel Process for Modifying Phararmacokinetics, Clin Pharmacokinet, 2001:40(7); 539-551.

10. Gregoriadis G. Chapter 14. Liposomes, Drug Carriers in Biology and Medicine, pp. 287-341 (Academic Press, 1979).

11. Drake T A, Morrissey J H, Edgington T S. Selective cellular expression of tissue factor in human tissues. Implications for disorders of hemostasis and thrombosis. Am J Pathol. 1989; 134:1087-1097.

12. Ruf W, Rehemtulla A, Morrissey J H, Edgington T S. Phospholipid-independent and -dependent interactions required for tissue factor receptor and cofactor function. J Biol Chem. 1991; 266:2158-2166.

13. Neuenschwander P F, Morrissey J H. Deletion of the membrane anchoring region of tissue factor abolishes autoactivation of factor VII but not cofactor function. Analysis of a mutant with a selective deficiency in activity. J Biol Chem. 1992; 267:14477-14482.

14. Paborsky L R, Caras I W, Fisher K L, Gorman C M. Lipid association, but not the transmembrane domain, is required for tissue factor activity. Substitution of the transmembrane domain with a phosphatidylinositol anchor. J Biol Chem. 1991; 266:21911-21916.

15. Macfarlane R G, Biggs R. A thrombin generation test; the application in haemophilia and thrombocytopenia. J Clin Pathol. 1953; 6:3-8.

16. Caen J, Bellucci S. The defective prothrombin consumption in Bernard-Soulier syndrome. Hypotheses from 1948 to 1982. Blood Cells. 1983; 9:389-399.

17. Rosing J, Bevers E M, Comfurius P, et al. Impaired factor X and prothrombin activation associated with decreased phospholipid exposure in platelets from a patient with a bleeding disorder. Blood. 1985; 65:1557-1561.

18. Reverter J C, Beguin S, Kessels H, Kumar R, Hemker H C, Coller B S. Inhibition of platelet-mediated, tissue factor-induced thrombin generation by the mouse/human chimeric 7E3 antibody. Potential implications for the effect of c7E3 Fab treatment on acute thrombosis and "clinical restenosis". J Clin Invest. 1996; 98:863-874.

19. Hemker H C, Al Dieri R, Beguin S. Thrombin generation assays: accruing clinical relevance. Curr Opin Hematol. 2004; 11:170-175.

20. Thomas L. Studies on the intravascular thromboplastin effect of tissue suspensions in mice: II. A factor in normal rabbit serum which inhibits the thromboplastin effect of the sedimentable tissue component. Bull Johns Hopkins Hosp. 1947; 81:26-42.

21. Gitel S N, Wessler S. The antithrombotic effects of warfarin and heparin following infusions of tissue thromboplastin in rabbits: clinical implications. J Lab Clin Med. 1979; 94:481-488.

22. Morrissey J H, Comp P C. Treatment of bleeding with modified tissue factor in combination with FVIIa. U.S. Pat. No. 5,374,617. 1994.

23. Thiagarajan P, Tait J F. Binding of annexin V/placental anticoagulant protein I to platelets. Evidence for phosphatidylserine exposure in the procoagulant response of activated platelets. J Biol Chem. 1990; 265:17420-17423.

24. Satta N, Toti F, Feugeas O, et al. Monocyte vesiculation is a possible mechanism for dissemination of membrane-associated procoagulant activities and adhesion molecules after stimulation by lipopolysaccharide. J Immunol. 1994; 153:3245-3255.

25. van Heerde W L, Poort S, van 't Veer C, Reutelingsperger C P, de Groot P G. Binding of recombinant annexin V to endothelial cells: effect of annexin V binding on endothelial-cell-mediated thrombin formation. Biochem J. 1994; 302 (Pt 1): 305-312.

26. Tait J F, Gibson D, Fujikawa K. Phospholipid binding properties of human placental anticoagulant protein-I, a member of the lipocortin family. J Biol Chem. 1989; 264: 7944-7949.

27. Neuenschwander P F, Bianco-Fisher E, Rezaie A R, Morrissey J H. Phosphatidylethanolamine augments factor VIIa-tissue factor activity: enhancement of sensitivity to phosphatidylserine. Biochemistry. 1995; 34:13988-13993.

28. Rezaie A R, Fiore M M, Neuenschwander P F, Esmon C T, Morrissey J H. Expression and purification of a soluble tissue factor fusion protein with an epitope for an unusual calcium-dependent antibody. Protein Expr Purif. 1992; 3:453-460.

29. Morrissey J H, Fair D S, Edgington T S. Monoclonal antibody analysis of purified and cell-associated tissue factor. Thromb Res. 1988; 52:247-261.

30. Gabriel N E, Roberts M F. Spontaneous formation of stable unilamellar vesicles. Biochemistry. 1984; 23:4011-4015.

31. Chen P S, Toribara TY, Warner H. Microdetermination of phosphorus. Analyt Chem. 1956; 28:1756-1758.

32. Mimms L T, Zampighi G, Nozaki Y, Tanford C, Reynolds J A. Phospholipid vesicle formation and transmembrane protein incorporation using octyl glucoside. Biochemistry. 1981; 20:833-840.

33. Neuenschwander P F, Fiore M M, Morrissey J H. Factor VII autoactivation proceeds via interaction of distinct protease-cofactor and zymogen-cofactor complexes. Implications of a two-dimensional enzyme kinetic mechanism. J Biol Chem. 1993; 268:21489-21492.

34. Kelley R F, Refino C J, O'Connell M P, et al. A soluble tissue factor mutant is a selective anticoagulant and antithrombotic agent. Blood. 1997; 89:3219-3227.

35. Tait J F, Engelhardt S, Smith C, Fujikawa K. Prourokinase-annexin V chimeras. Construction, expression, and characterization of recombinant proteins. J Biol Chem. 1995; 270:21594-21599.

36. Rand J H, Wu X X, Lapinski R, et al. Detection of antibody-mediated reduction of annexin A5 anticoagulant activity in plasmas of patients with the antiphospholipid syndrome. Blood. 2004; 104:2783-2790.

37. Huang Q, Neuenschwander P F, Rezaie A R, Morrissey J H. Substrate recognition by tissue factor-factor VIIa. Evidence for interaction of residues Lys165 and Lys166 of tissue factor with the 4-carboxyglutamate-rich domain of factor X. J Biol Chem. 1996; 271:21752-21757.

38. Yamamoto M, Nakagaki T, Kisiel W. Tissue factor-dependent autoactivation of human blood coagulation factor VII. J Biol Chem. 1992; 267:19089-19094.

39. Fiore M M, Neuenschwander P F, Morrissey J H. The biochemical basis for the apparent defect of soluble mutant tissue factor in enhancing the proteolytic activities of factor VIIa. J Biol Chem. 1994; 269:143-149.

40. Morrissey J H, Neuenschwander P F, Huang Q, McCallum C D, Su B, Johnson A E. Factor VIIa-tissue factor: functional importance of protein-membrane interactions. Thromb Haemost. 1997; 78:112-116.

41. al Dieri R, Alban S, Beguin S, Hemker H C. Thrombin generation for the control of heparin treatment, comparison with the activated partial thromboplastin time. J Thromb Haemost. 2004; 2:1395-1401.

42. Hedner U. Dosing with recombinant factor viia based on current evidence. Semin Hematol. 2004; 41:35-39.

43. Dejana E, Quintana A, Callioni A, de Gaetano G. Bleeding time in laboratory animals. III—Do tail bleeding times in rats only measure a platelet defect? (the aspirin puzzle). Thromb Res. 1979; 15:199-207.

44. Dejana E, Callioni A, Quintana A, de Gaetano G. Bleeding time in laboratory animals. II—A comparison of different assay conditions in rats. Thromb Res. 1979; 15:191-197.

45. Diness V, Lund-Hansen T, Hedner U. Effect of recombinant human FVIIA on warfarin-induced bleeding in rats. Thromb Res. 1990; 59:921-929.

46. Kung S H, Hagstrom J N, Cass D, et al. Human factor IX corrects the bleeding diathesis of mice with hemophilia B. Blood. 1998; 91:784-790.

47. Waxman E, Ross J B, Laue T M, et al. Tissue factor and its extracellular soluble domain: the relationship between intermolecular association with factor VIIa and enzymatic activity of the complex. Biochemistry. 1992; 31:3998-4003.

48. Huang X, Molema G, King S, Watkins L, Edgington T S, Thorpe P E. Tumor infarction in mice by antibody-directed targeting of tissue factor to tumor vasculature. Science. 1997; 275:547-550.

49. Ran S, Gao B, Duffy S, Watkins L, Rote N, Thorpe P E. Infarction of solid Hodgkin's tumors in mice by antibody-directed targeting of tissue factor to tumor vasculature. Cancer Res. 1998; 58:4646-4653.

50. Nilsson F, Kosmehl H, Zardi L, Neri D. Targeted delivery of tissue factor to the ED-B domain of fibronectin, a marker of angiogenesis, mediates the infarction of solid tumors in mice. Cancer Res. 2001; 61:711-716.

51. Liu C, Huang H, Donate F, et al. Prostate-specific membrane antigen directed selective thrombotic infarction of tumors. Cancer Res. 2002; 62:5470-5475.

52. Hu P, Yan J, Sharifi J, Bai T, Khawli L A, Epstein A L. Comparison of three different targeted tissue factor fusion proteins for inducing tumor vessel thrombosis. Cancer Res. 2003; 63:5046-5053.

53. Tranholm M, Kristensen K, Kristensen A T, Pyke C, Rojkjaer R, Persson E. Improved hemostasis with superactive analogs of factor VIIa in a mouse model of hemophilia A. Blood. 2003; 102:3615-3620.

54. Schatz S, Turecek P L, Fiedler C, et al. Evaluation of the haemostatic potential of factor VIII-heparin cofactor II hybrid proteins in a mouse model. Br J Haematol. 2003; 123:692-695.

55. Nelsestuen G L, Stone M, Martinez M B, Harvey S B, Foster D, Kisiel W. Elevated function of blood clotting factor VIIa mutants that have enhanced affinity for membranes. Behavior in a diffusion-limited reaction. J Biol Chem. 2001; 276:39825-39831.

56. Rippmann J F, Pfizenmaier K, Mattes R, Rettig W J, Moosmayer D. Fusion of the tissue factor extracellular domain to a tumour stroma specific single-chain fragment variable antibody results in an antigen-specific coagulation-promoting molecule. Biochem J. 2000; 349 Pt 3:805-812.

57. Ran S, Thorpe P E. Phosphatidylserine is a marker of tumor vasculature and a potential target for cancer imaging and therapy. Int J Radiat Oncol Biol Phys. 2002; 54:1479-1484.

58. Ran S, Downes A, Thorpe P E. Increased exposure of anionic phospholipids on the surface of tumor blood vessels. Cancer Res. 2002; 62:6132-6140.

59. Belhocine T, Steinmetz N, Hustinx R, et al. Increased uptake of the apoptosis-imaging agent (99m)Tc recombinant human Annexin V in human tumors after one course of chemotherapy as a predictor of tumor response and patient prognosis. Clin Cancer Res. 2002; 8:2766-2774.

60. Mochizuki T, Kuge Y, Zhao S, et al. Detection of Apoptotic Tumor Response In Vivo After a Single Dose of Chemotherapy with (99m)Tc-Annexin V. J Nucl Med. 2003; 44:92-97.

61. Takei T, Kuge Y, Zhao S, et al. Time Course of Apoptotic Tumor Response After a Single Dose of Chemotherapy: Comparison with 99 mTc-Annexin V Uptake and Histologic Findings in an Experimental Model. J Nucl Med. 2004; 45:2083-2087.

62. Paris F, Fuks Z, Kang A, et al. Endothelial apoptosis as the primary lesion initiating intestinal radiation damage in mice. Science. 2001; 293:293-297.

What is claimed is:

1. A method of inducing hemostasis or thrombosis in a human patient having a bleeding disorder, comprising:

providing a chimeric protein comprising a phosphatidylserine-binding Annexin and a soluble tissue factor domain comprising SEQ ID NO:2 or a mutant thereof having human Tissue Factor activity; and administering the chimeric protein to the patient in an amount effective to promote coagulation in a vascularized area of the patient, wherein the vascularized area is non-cancerous.

2. The method of claim 1 wherein the phosphatidylserine-binding Annexin is human Annexin V.

3. The method of claim 1 wherein the chimeric protein mutant of SEQ ID NO:2 comprises at least one substitution selected from the group consisting of ala at position 13, 131, 163, 164, or 183, asn at position 42, or 138, trp at position 48, ser at position 52, asp at position 128, gln at position 129, 163, or 164, and glu at position 163 or 164.

4. The method of claim 1 wherein the chimeric protein further consists of a peptide consisting of gly and/or ser amino acid residues linked to the amino terminal end of the SEQ ID NO:2 portion of the chimeric protein.

5. The method of claim 1 wherein the chimeric protein further comprises a peptide linker comprising gly and/or ser amino acid residues connecting the soluble tissue factor domain and the phosphatidylserine-binding Annexin.

6. The method of claim 1 wherein the bleeding disorder is due to presence of an anticoagulant drug; a lack of a coagulation factor due to trauma, transfusion, antibodies, or congenital conditions; liver disease; vascular or head injury; gastrointestinal conditions including gastritis, ulcer, and esophageal varices; cystitis, endometritis; or bleeding due to insufficient platelets or improperly functioning platelets.

7. The method of claim 1 further comprising administering the chimeric protein with recombinant Factor VIIa.

8. The method of claim 1 wherein the vascularized area comprises a telangiectasia, arterial malformation, venous malformation, capillary malformation, lymphatic malformation, arterio-venous malformation, hemangioma, or aneurysm.

9. The method of claim 1 wherein the chimeric protein is administered locally in order to induce a local thrombosis.

10. The method of claim 1 further comprising administering a drug, chemical, electrical stimulus or radiation in adjunct to the step of administering the chimeric protein.

11. The method of claim 1 wherein the chimeric protein further comprises a therapeutic compound or material wherein the chimeric protein serves to deliver the therapeutic compound or material to a site in need of treatment therewith.

12. The method of claim 11 wherein the vascularized area to which the therapeutic compound or material is delivered is a tumor or abnormal vascular bed.

13. The method of claim 11 wherein the therapeutic material or compound is chemotherapeutic or radioactive.

* * * * *

UNITED STATES PATENT AND TRADEMARK OFFICE

CERTIFICATE OF CORRECTION

PATENT NO. : 7,807,644 B2
APPLICATION NO. : 12/157525
DATED : October 5, 2010
INVENTOR(S) : Stuart E. Lind, Wei-Qun Ding and Roger G. Harrison It is certified that error appears in the above-identified patent and that said Letters Patent is hereby corrected as shown below:

Column 2, line 33: Delete "(sTFM-" and replace with -- (sTFAA- --.
Column 5, line 10: Delete "gin" and replace with -- gln --.
Column 8, line 46: Delete "(sTFM-annV)" and replace with -- (sTFAA-annV) --.
Column 8, line 53: Delete "sTFM-annV" and replace with -- sTFAA-annV --.
Column 9, line 55: Delete "sTFM- " and replace with -- sTFAA- --.
Column 11, line 6: Delete "sTFM-annV)" and replace with -- sTFAA-annV) --.
Column 11, line 66: Delete "sTFM-annV" and replace with -- sTFAA-annV --.
Column 12, line 7: Delete "sTFM-annV" and replace with -- sTFAA-annV --.
Column 12, line 10: Delete "sTFM-annV" and replace with -- sTFAA-annV --.
Column 12, line 11: Delete "sTFM," and replace with -- sTFAA, --.

Signed and Sealed this
Twenty-second Day of February, 2011

David J. Kappos
*Director of the United States Patent and Trademark Office*

SEQUENCE LISTING

```
<160> NUMBER OF SEQ ID NOS: 28

<210> SEQ ID NO 1
<211> LENGTH: 651
<212> TYPE: DNA
<213> ORGANISM: Homo sapiens
```

-continued

<400> SEQUENCE: 1

```
actacaaata ctgtggcagc atataattta acttggaaat caactaattt caagacaatt     60
ttggagtggg aacccaaacc cgtcaatcaa gtctacactg ttcaaataag cactaagtca    120
ggagattgga aaagcaaatg cttttacaca acagacacag agtgtgacct caccgacgag    180
attgtgaagg atgtgaagca gacgtacttg gcacgggtct tctcctaccc ggcagggaat    240
gtggagagca ccggttctgc tggggagcct ctgtatgaga actccccaga gttcacacct    300
tacctggaga caaacctcgg acagccaaca attcagagtt ttgaacaggt gggaacaaaa    360
gtgaatgtga ccgtagaaga tgaacggact ttagtcagaa ggaacaacac tttcctaagc    420
ctccgggatg tttttggcaa ggacttaatt tatacacttt attattggaa atcttcaagt    480
tcaggagccg caacagccaa aacaaacact aatgagtttt tgattgatgt ggataaagga    540
gaaaactact gtttcagtgt tcaagcagtg attccctccc gaacagttaa ccggaagagt    600
acagacagcc cggtagagtg tatgggccag gagaaagggg aattcagaga a             651
```

<210> SEQ ID NO 2
<211> LENGTH: 217
<212> TYPE: PRT
<213> ORGANISM: Homo sapiens

<400> SEQUENCE: 2

```
Thr Thr Asn Thr Val Ala Ala Tyr Asn Leu Thr Trp Lys Ser Thr Asn
1               5                   10                  15

Phe Lys Thr Ile Leu Glu Trp Glu Pro Lys Pro Val Asn Gln Val Tyr
            20                  25                  30

Thr Val Gln Ile Ser Thr Lys Ser Gly Asp Trp Lys Ser Lys Cys Phe
        35                  40                  45

Tyr Thr Thr Asp Thr Glu Cys Asp Leu Thr Asp Glu Ile Val Lys Asp
    50                  55                  60

Val Lys Gln Thr Tyr Leu Ala Arg Val Phe Ser Tyr Pro Ala Gly Asn
65                  70                  75                  80

Val Glu Ser Thr Gly Ser Ala Gly Glu Pro Leu Tyr Glu Asn Ser Pro
                85                  90                  95

Glu Phe Thr Pro Tyr Leu Glu Thr Asn Leu Gly Gln Pro Thr Ile Gln
            100                 105                 110

Ser Phe Glu Gln Val Gly Thr Lys Val Asn Val Thr Val Glu Asp Glu
        115                 120                 125

Arg Thr Leu Val Arg Arg Asn Asn Thr Phe Leu Ser Leu Arg Asp Val
    130                 135                 140

Phe Gly Lys Asp Leu Ile Tyr Thr Leu Tyr Tyr Trp Lys Ser Ser Ser
145                 150                 155                 160

Ser Gly Ala Ala Thr Ala Lys Thr Asn Thr Asn Glu Phe Leu Ile Asp
                165                 170                 175

Val Asp Lys Gly Glu Asn Tyr Cys Phe Ser Val Gln Ala Val Ile Pro
            180                 185                 190

Ser Arg Thr Val Asn Arg Lys Ser Thr Asp Ser Pro Val Glu Cys Met
        195                 200                 205

Gly Gln Glu Lys Gly Glu Phe Arg Glu
    210                 215
```

<210> SEQ ID NO 3
<211> LENGTH: 957
<212> TYPE: DNA
<213> ORGANISM: Homo sapiens -continued

<400> SEQUENCE: 3

```
gcacaggttc tcagaggcac tgtgactgac ttccctggat ttgatgagcg ggctgatgca     60
gaaactcttc ggaaggctat gaaaggcttg ggcacagatg aggagagcat cctgactctg    120
ttgacatccc gaagtaatgc tcagcgccag gaaatctctg cagcttttaa gactctgttt    180
ggcagggatc ttctggatga cctgaaatca gaactaactg gaaaatttga aaaattaatt    240
gtggctctga tgaaaccctc tcggctttat gatgcttatg aactgaaaca tgccttgaag    300
ggagctggaa caaatgaaaa agtactgaca gaaattattg cttcaaggac acctgaagaa    360
ctgagagcca tcaaacaagt ttatgaagaa gaatatggct caagcctgga agatgacgtg    420
gtgggggaca cttcagggta ctaccagcgg atgttggtgg ttctccttca ggctaacaga    480
gaccctgatg ctggaattga tgaagctcaa gttgaacaag atgctcaggc tttatttcag    540
gctggagaac ttaaatgggg gacagatgaa gaaaagttta tcaccatctt tggaacacga    600
agtgtgtctc atttgagaaa ggtgtttgac aagtacatga ctatatcagg atttcaaatt    660
gaggaaacca ttgaccgcga gacttctggc aatttagagc aactactcct tgctgttgtg    720
aaatctattc gaagtatacc tgcctacctt gcagagaccc tctattatgc tatgaaggga    780
gctgggacag atgatcatac cctcatcaga gtcatggttt ccaggagtga gattgatctg    840
tttaacatca ggaaggagtt taggaagaat tttgccacct ctctttattc catgattaag    900
ggagatacat ctggggacta taagaaagct cttctgctgc tctgtggaga agatgac       957
```

<210> SEQ ID NO 4
<211> LENGTH: 319
<212> TYPE: PRT
<213> ORGANISM: Homo sapiens

<400> SEQUENCE: 4

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190
```

-continued

```
Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Cys Gly Glu Asp Asp
305                 310                 315


<210> SEQ ID NO 5
<211> LENGTH: 45
<212> TYPE: DNA
<213> ORGANISM: Homo sapiens

<400> SEQUENCE: 5

ggtggaggcg gttcaggcgg tggaggttca ggaggtggcg gatca                      45


<210> SEQ ID NO 6
<211> LENGTH: 15
<212> TYPE: PRT
<213> ORGANISM: Homo sapiens

<400> SEQUENCE: 6

Gly Gly Gly Gly Ser Gly Gly Gly Gly Ser Gly Gly Gly Gly Ser
1               5                   10                  15


<210> SEQ ID NO 7
<211> LENGTH: 29
<212> TYPE: DNA
<213> ORGANISM: Homo sapiens

<400> SEQUENCE: 7

ccgctcgaga ccaccaccac caccactga                                        29


<210> SEQ ID NO 8
<211> LENGTH: 9
<212> TYPE: PRT
<213> ORGANISM: Homo sapiens

<400> SEQUENCE: 8

Pro Leu Glu His His His His His His
1               5


<210> SEQ ID NO 9
<211> LENGTH: 652
<212> TYPE: DNA
<213> ORGANISM: Homo sapiens

<400> SEQUENCE: 9

actacaaata ctgtggcagc atataattta acttggaaat caactaattt caagacaatt      60

ttggagtggg aacccaaacc cgtcaatcaa gtctacactg ttcaaataag cactaagtca     120

ggagattgga aaagcaaatg cttttacaca acagacacag agtgtgacct caccgacgag     180
```

-continued

```
attgtgaagg atgtgaagca gacgtacttg gcacgggtct tctcctaccc ggcagggaat    240

gtggagagca ccggttctgc tggggagcct ctgtatgaga actccccaga gttcacacct    300

tacctggaga caaacctcgg acagccaaca attcagagtt ttgaacaggt gggaacaaaa    360

gtgaatgtga ccgtagaaga tgaacggact ttagtcagaa ggaacaacac tttcctaagc    420

ctccgggatg tttttggcaa ggacttaatt tatacacttt attattggaa atcttcaagt    480

tcaggaagcc gcaacagcca aaacaaacac taatgagttt ttgattgatg tggataaagg    540

agaaaactac tgtttcagtg ttcaagcagt gattccctcc cgaacagtta accggaagag    600

tacagacagc ccggtagagt gtatgggcca ggagaaaggg gaattcagag aa            652
```

```
<210> SEQ ID NO 10
<211> LENGTH: 217
<212> TYPE: PRT
<213> ORGANISM: Homo sapiens

<400> SEQUENCE: 10

Thr Thr Asn Thr Val Ala Ala Tyr Asn Leu Thr Trp Lys Ser Thr Asn
1               5                   10                  15

Phe Lys Thr Ile Leu Glu Trp Glu Pro Lys Pro Val Asn Gln Val Tyr
            20                  25                  30

Thr Val Gln Ile Ser Thr Lys Ser Gly Asp Trp Lys Ser Lys Cys Phe
        35                  40                  45

Tyr Thr Thr Asp Thr Glu Cys Asp Leu Thr Asp Glu Ile Val Lys Asp
    50                  55                  60

Val Lys Gln Thr Tyr Leu Ala Arg Val Phe Ser Tyr Pro Ala Gly Asn
65                  70                  75                  80

Val Glu Ser Thr Gly Ser Ala Gly Glu Pro Leu Tyr Glu Asn Ser Pro
                85                  90                  95

Glu Phe Thr Pro Tyr Leu Glu Thr Asn Leu Gly Gln Pro Thr Ile Gln
            100                 105                 110

Ser Phe Glu Gln Val Gly Thr Lys Val Asn Val Thr Val Glu Asp Glu
        115                 120                 125

Arg Thr Leu Val Arg Arg Asn Asn Thr Phe Leu Ser Leu Arg Asp Val
    130                 135                 140

Phe Gly Lys Asp Leu Ile Tyr Thr Leu Tyr Tyr Trp Lys Ser Ser Ser
145                 150                 155                 160

Ser Gly Ala Ala Thr Ala Lys Thr Asn Thr Asn Glu Ala Ala Ile Asp
                165                 170                 175

Val Asp Lys Gly Glu Asn Tyr Cys Phe Ser Val Gln Ala Val Ile Pro
            180                 185                 190

Ser Arg Thr Val Asn Arg Lys Ser Thr Asp Ser Pro Val Glu Cys Met
        195                 200                 205

Gly Gln Glu Lys Gly Glu Phe Arg Glu
    210                 215
```

```
<210> SEQ ID NO 11
<211> LENGTH: 652
<212> TYPE: DNA
<213> ORGANISM: Homo sapiens

<400> SEQUENCE: 11

actacaaata ctgtggcagc atataattta acttggaaat caactaattt caagacaatt     60

ttggagtggg aacccaaacc cgtcaatcaa gtctacactg ttcaaataag cactaagtca    120
```

-continued

```
ggagattgga aaagcaaatg cttttacaca acagacacag agtgtgacct caccgacgag    180

attgtgaagg atgtgaagca gacgtacttg gcacgggtct tctcctaccc ggcagggaat    240

gtggagagca ccggttctgc tggggagcct ctgtatgaga actccccaga gttcacacct    300

tacctggaga caaacctcgg acagccaaca attcagagtt ttgaacaggt gggaacaaaa    360

gtgaatgtga ccgtagaaga tgaacggact ttagtcagaa ggaacaacac tttcctaagc    420

ctccgggatg tttttggcaa ggacttaatt tatacacttt attattggaa atcttcaagt    480

tcaggaagaa gagacagcca aaacaaacac taatgagttt ttgattgatg tggataaagg    540

agaaaactac tgtttcagtg ttcaagcagt gattccctcc cgaacagtta accggaagag    600

tacagacagc ccggtagagt gtatgggcca ggagaaaggg gaattcagag aa            652


<210> SEQ ID NO 12
<211> LENGTH: 217
<212> TYPE: PRT
<213> ORGANISM: Homo sapiens

<400> SEQUENCE: 12

Thr Thr Asn Thr Val Ala Ala Tyr Asn Leu Thr Trp Lys Ser Thr Asn
1               5                   10                  15

Phe Lys Thr Ile Leu Glu Trp Glu Pro Lys Pro Val Asn Gln Val Tyr
            20                  25                  30

Thr Val Gln Ile Ser Thr Lys Ser Gly Asp Trp Lys Ser Lys Cys Phe
        35                  40                  45

Tyr Thr Thr Asp Thr Glu Cys Asp Leu Thr Asp Glu Ile Val Lys Asp
    50                  55                  60

Val Lys Gln Thr Tyr Leu Ala Arg Val Phe Ser Tyr Pro Ala Gly Asn
65                  70                  75                  80

Val Glu Ser Thr Gly Ser Ala Gly Glu Pro Leu Tyr Glu Asn Ser Pro
                85                  90                  95

Glu Phe Thr Pro Tyr Leu Glu Thr Asn Leu Gly Gln Pro Thr Ile Gln
            100                 105                 110

Ser Phe Glu Gln Val Gly Thr Lys Val Asn Val Thr Val Glu Asp Glu
        115                 120                 125

Arg Thr Leu Val Arg Arg Asn Asn Thr Phe Leu Ser Leu Arg Asp Val
    130                 135                 140

Phe Gly Lys Asp Leu Ile Tyr Thr Leu Tyr Tyr Trp Lys Ser Ser Ser
145                 150                 155                 160

Ser Gly Glu Glu Thr Ala Lys Thr Asn Thr Asn Glu Ala Ala Ile Asp
                165                 170                 175

Val Asp Lys Gly Glu Asn Tyr Cys Phe Ser Val Gln Ala Val Ile Pro
            180                 185                 190

Ser Arg Thr Val Asn Arg Lys Ser Thr Asp Ser Pro Val Glu Cys Met
        195                 200                 205

Gly Gln Glu Lys Gly Glu Phe Arg Glu
    210                 215


<210> SEQ ID NO 13
<211> LENGTH: 652
<212> TYPE: DNA
<213> ORGANISM: Homo sapiens

<400> SEQUENCE: 13

actacaaata ctgtggcagc atataattta acttggaaat caactaattt caagacaatt     60

ttggagtggg aacccaaacc cgtcaatcaa gtctacactg ttcaaataag cactaagtca    120
```

-continued

```
ggagattgga aaagcaaatg cttttacaca acagacacag agtgtgacct caccgacgag    180

attgtgaagg atgtgaagca gacgtacttg gcacgggtct tctcctaccc ggcagggaat    240

gtggagagca ccggttctgc tggggagcct ctgtatgaga actccccaga gttcacacct    300

tacctggaga caaacctcgg acagccaaca attcagagtt ttgaacaggt gggaacaaaa    360

gtgaatgtga ccgtagaaga tgaacggact ttagtcagaa ggaacaacac tttcctaagc    420

ctccgggatg tttttggcaa ggacttaatt tatacacttt attattggaa atcttcaagt    480

tcaggaacaa cagacagcca aaacaaacac taatgagttt ttgattgatg tggataaagg    540

agaaaactac tgtttcagtg ttcaagcagt gattccctcc cgaacagtta accggaagag    600

tacagacagc ccggtagagt gtatgggcca ggagaaaggg gaattcagag aa            652
```

```
<210> SEQ ID NO 14
<211> LENGTH: 217
<212> TYPE: PRT
<213> ORGANISM: Homo sapiens

<400> SEQUENCE: 14

Thr Thr Asn Thr Val Ala Ala Tyr Asn Leu Thr Trp Lys Ser Thr Asn
1               5                   10                  15

Phe Lys Thr Ile Leu Glu Trp Glu Pro Lys Pro Val Asn Gln Val Tyr
            20                  25                  30

Thr Val Gln Ile Ser Thr Lys Ser Gly Asp Trp Lys Ser Lys Cys Phe
        35                  40                  45

Tyr Thr Thr Asp Thr Glu Cys Asp Leu Thr Asp Glu Ile Val Lys Asp
    50                  55                  60

Val Lys Gln Thr Tyr Leu Ala Arg Val Phe Ser Tyr Pro Ala Gly Asn
65                  70                  75                  80

Val Glu Ser Thr Gly Ser Ala Gly Glu Pro Leu Tyr Glu Asn Ser Pro
                85                  90                  95

Glu Phe Thr Pro Tyr Leu Glu Thr Asn Leu Gly Gln Pro Thr Ile Gln
            100                 105                 110

Ser Phe Glu Gln Val Gly Thr Lys Val Asn Val Thr Val Glu Asp Glu
        115                 120                 125

Arg Thr Leu Val Arg Arg Asn Asn Thr Phe Leu Ser Leu Arg Asp Val
    130                 135                 140

Phe Gly Lys Asp Leu Ile Tyr Thr Leu Tyr Tyr Trp Lys Ser Ser Ser
145                 150                 155                 160

Ser Gly Gln Gln Thr Ala Lys Thr Asn Thr Asn Glu Ala Ala Ile Asp
                165                 170                 175

Val Asp Lys Gly Glu Asn Tyr Cys Phe Ser Val Gln Ala Val Ile Pro
            180                 185                 190

Ser Arg Thr Val Asn Arg Lys Ser Thr Asp Ser Pro Val Glu Cys Met
        195                 200                 205

Gly Gln Glu Lys Gly Glu Phe Arg Glu
    210                 215


<210> SEQ ID NO 15
<211> LENGTH: 39
<212> TYPE: DNA
<213> ORGANISM: Homo sapiens

<400> SEQUENCE: 15

ctcggaggta gtggcatcta ccgtagccga tcactagag                            39
```

-continued

<210> SEQ ID NO 16
<211> LENGTH: 12
<212> TYPE: PRT
<213> ORGANISM: Homo sapiens

<400> SEQUENCE: 16

Leu Gly Gly Ser Gly Ile Tyr Arg Ser Arg Ser Leu
1 5 10

<210> SEQ ID NO 17
<211> LENGTH: 18
<212> TYPE: DNA
<213> ORGANISM: Homo sapiens

<400> SEQUENCE: 17
ctcgttcctc gtggaagt 18

<210> SEQ ID NO 18
<211> LENGTH: 6
<212> TYPE: PRT
<213> ORGANISM: Homo sapiens

<400> SEQUENCE: 18

Leu Val Pro Arg Gly Ser
1 5

<210> SEQ ID NO 19
<211> LENGTH: 2400
<212> TYPE: DNA
<213> ORGANISM: Homo sapiens

<400> SEQUENCE: 19
ggcactacaa atactgtggc agcatataat ttaacttgga aatcaactaa tttcaagaca 60
attttggagt gggaacccaa acccgtcaat caagtctaca ctgttcaaat aagcactaag 120
tcaggagatt ggaaaagcaa atgcttttac acaacagaca cagagtgtga cctcaccgac 180
gagattgtga aggatgtgaa gcagacgtac ttggcacggg tcttctccta cccggcaggg 240
aatgtggaga gcaccggttc tgctggggag cctctgtatg agaactcccc agagttcaca 300
ccttacctgg agacaaacct cggacagcca acaattcaga gttttgaaca ggtgggaaca 360
aaagtgaatg tgaccgtaga agatgaacgg actttagtca gaaggaacaa cactttccta 420
agcctccggg atgtttttgg caaggactta atttatacac tttattattg gaaatcttca 480
agttcaggaa agaaaacagc caaaacaaac actaatgagt ttttgattga tgtggataaa 540
ggagaaaact actgtttcag tgttcaagca gtgattccct cccgaacagt taaccggaag 600
agtacagaca gcccggtaga gtgtatgggc caggagaaag ggaattcag agaaggtgga 660 ggcggttcag gcggtggagg ttcaggaggt ggcggatcaa agcttggcgc ttcaggcact 720
acaaatactg tggcagcata taatttaact tggaaatcaa ctaatttcaa gacaattttg 780
gagtgggaac ccaaacccgt caatcaagtc tacactgttc aaataagcac taagtcagga 840
gattggaaaa gcaaatgctt ttacacaaca gacacagagt gtgacctcac cgacgagatt 900
gtgaaggatg tgaagcagac gtacttggca cgggtcttct cctacccggc agggaatgtg 960
gagagcaccg gttctgctgg ggagcctctg tatgagaact ccccagagtt cacaccttac 1020
ctggagacaa acctcggaca gccaacaatt cagagttttg aacaggtggg aacaaaagtg 1080
aatgtgaccg tagaagatga acggacttta gtcagaagga acaacacttt cctaagcctc 1140
cgggatgttt ttggcaagga cttaatttat acactttatt attggaaatc ttcaagttca 1200

-continued

```
ggaaagaaaa cagccaaaac aaacactaat gagtttttga ttgatgtgga taaaggagaa   1260

aactactgtt tcagtgttca agcagtgatt ccctcccgaa cagttaaccg gaagagtaca   1320

gacagcccgg tagagtgtat gggccaggag aaaggggaat tcagagaagg tggaggcggt   1380

tcaggcggtg gaggttcagg aggtggcgga tcagcacagg ttctcagagg cactgtgact   1440

gacttccctg gatttgatga gcgggctgat gcagaaactc ttcggaaggc tatgaaaggc   1500

ttgggcacag atgaggagag catcctgact ctgttgacat cccgaagtaa tgctcagcgc   1560

caggaaatct ctgcagcttt taagactctg tttggcaggg atcttctgga tgacctgaaa   1620

tcagaactaa ctggaaaatt tgaaaaatta attgtggctc tgatgaaacc ctctcggctt   1680

tatgatgctt atgaactgaa acatgccttg aagggagctg gaacaaatga aaaagtactg   1740

acagaaatta ttgcttcaag gacacctgaa gaactgagag ccatcaaaca agtttatgaa   1800

gaagaatatg gctcaagcct ggaagatgac gtggtggggg acacttcagg gtactaccag   1860

cggatgttgg tggttctcct tcaggctaac agagaccctg atgctggaat tgatgaagct   1920

caagttgaac aagatgctca ggctttattt caggctggag aacttaaatg gggacagat   1980

gaagaaaagt ttatcaccat ctttggaaca cgaagtgtgt ctcatttgag aaaggtgttt   2040

gacaagtaca tgactatatc aggatttcaa attgaggaaa ccattgaccg cgagacttct   2100

ggcaatttag agcaactact ccttgctgtt gtgaaatcta ttcgaagtat acctgcctac   2160

cttgcagaga ccctctatta tgctatgaag ggagctggga cagatgatca taccctcatc   2220

agagtcatgg tttccaggag tgagattgat ctgtttaaca tcaggaagga gtttaggaag   2280

aattttgcca cctctcttta ttccatgatt aagggagata catctgggga ctataagaaa   2340

gctcttctgc tgctctgtgg agaagatgac ccgctcgagc accaccacca ccaccactga   2400
```

<210> SEQ ID NO 20
<211> LENGTH: 804
<212> TYPE: PRT
<213> ORGANISM: Homo sapiens

<400> SEQUENCE: 20

```
Met Ala Gly Ala Ser Gly Thr Thr Asn Thr Val Ala Ala Tyr Asn Leu
1               5                   10                  15

Thr Trp Lys Ser Thr Asn Phe Lys Thr Ile Leu Glu Trp Glu Pro Lys
            20                  25                  30

Pro Val Asn Gln Val Tyr Thr Val Gln Ile Ser Thr Lys Ser Gly Asp
        35                  40                  45

Trp Lys Ser Lys Cys Phe Tyr Thr Thr Asp Thr Glu Cys Asp Leu Thr
    50                  55                  60

Asp Glu Ile Val Lys Asp Val Lys Gln Thr Tyr Leu Ala Arg Val Phe
65                  70                  75                  80

Ser Tyr Pro Ala Gly Asn Val Glu Ser Thr Gly Ser Ala Gly Glu Pro
                85                  90                  95

Leu Tyr Glu Asn Ser Pro Glu Phe Thr Pro Tyr Leu Glu Thr Asn Leu
            100                 105                 110

Gly Gln Pro Thr Ile Gln Ser Phe Glu Gln Val Gly Thr Lys Val Asn
        115                 120                 125

Val Thr Val Glu Asp Glu Arg Thr Leu Val Arg Arg Asn Asn Thr Phe
    130                 135                 140

Leu Ser Leu Arg Asp Val Phe Gly Lys Asp Leu Ile Tyr Thr Leu Tyr
145                 150                 155                 160
```

-continued

```
Tyr Trp Lys Ser Ser Ser Ser Gly Lys Lys Thr Ala Lys Thr Asn Thr
                165                 170                 175

Asn Glu Phe Leu Ile Asp Val Asp Lys Gly Glu Asn Tyr Cys Phe Ser
            180                 185                 190

Val Gln Ala Val Ile Pro Ser Arg Thr Val Asn Arg Lys Ser Thr Asp
        195                 200                 205

Ser Pro Val Glu Cys Met Gly Gln Glu Lys Gly Glu Phe Arg Glu Gly
    210                 215                 220

Gly Gly Gly Ser Gly Gly Gly Gly Ser Gly Gly Gly Gly Ser Lys Leu
225                 230                 235                 240

Gly Ala Ser Gly Thr Thr Asn Thr Val Ala Ala Tyr Asn Leu Thr Trp
                245                 250                 255

Lys Ser Thr Asn Phe Lys Thr Ile Leu Glu Trp Glu Pro Lys Pro Val
            260                 265                 270

Asn Gln Val Tyr Thr Val Gln Ile Ser Thr Lys Ser Gly Asp Trp Lys
        275                 280                 285

Ser Lys Cys Phe Tyr Thr Thr Asp Thr Glu Cys Asp Leu Thr Asp Glu
    290                 295                 300

Ile Val Lys Asp Val Lys Gln Thr Tyr Leu Ala Arg Val Phe Ser Tyr
305                 310                 315                 320

Pro Ala Gly Asn Val Glu Ser Thr Gly Ser Ala Gly Glu Pro Leu Tyr
                325                 330                 335

Glu Asn Ser Pro Glu Phe Thr Pro Tyr Leu Glu Thr Asn Leu Gly Gln
            340                 345                 350

Pro Thr Ile Gln Ser Phe Glu Gln Val Gly Thr Lys Val Asn Val Thr
        355                 360                 365

Val Glu Asp Glu Arg Thr Leu Val Arg Arg Asn Asn Thr Phe Leu Ser
    370                 375                 380

Leu Arg Asp Val Phe Gly Lys Asp Leu Ile Tyr Thr Leu Tyr Tyr Trp
385                 390                 395                 400

Lys Ser Ser Ser Ser Gly Lys Lys Thr Ala Lys Thr Asn Thr Asn Glu
                405                 410                 415

Phe Leu Ile Asp Val Asp Lys Gly Glu Asn Tyr Cys Phe Ser Val Gln
            420                 425                 430

Ala Val Ile Pro Ser Arg Thr Val Asn Arg Lys Ser Thr Asp Ser Pro
        435                 440                 445

Val Glu Cys Met Gly Gln Glu Lys Gly Glu Phe Arg Glu Gly Gly Gly
    450                 455                 460

Gly Ser Gly Gly Gly Gly Ser Gly Gly Gly Gly Ser Ala Gln Val Leu
465                 470                 475                 480

Arg Gly Thr Val Thr Asp Phe Pro Gly Phe Asp Glu Arg Ala Asp Ala
                485                 490                 495

Glu Thr Leu Arg Lys Ala Met Lys Gly Leu Gly Thr Asp Glu Glu Ser
            500                 505                 510

Ile Leu Thr Leu Leu Thr Ser Arg Ser Asn Ala Gln Arg Gln Glu Ile
        515                 520                 525

Ser Ala Ala Phe Lys Thr Leu Phe Gly Arg Asp Leu Leu Asp Asp Leu
    530                 535                 540

Lys Ser Glu Leu Thr Gly Lys Phe Glu Lys Leu Ile Val Ala Leu Met
545                 550                 555                 560

Lys Pro Ser Arg Leu Tyr Asp Ala Tyr Glu Leu Lys His Ala Leu Lys
                565                 570                 575

Gly Ala Gly Thr Asn Glu Lys Val Leu Thr Glu Ile Ile Ala Ser Arg
```

-continued

```
            580                 585                 590

Thr Pro Glu Glu Leu Arg Ala Ile Lys Gln Val Tyr Glu Glu Glu Tyr
        595                 600                 605

Gly Ser Ser Leu Glu Asp Asp Val Val Gly Asp Thr Ser Gly Tyr Tyr
    610                 615                 620

Gln Arg Met Leu Val Val Leu Leu Gln Ala Asn Arg Asp Pro Asp Ala
625                 630                 635                 640

Gly Ile Asp Glu Ala Gln Val Glu Gln Asp Ala Gln Ala Leu Phe Gln
                645                 650                 655

Ala Gly Glu Leu Lys Trp Gly Thr Asp Glu Glu Lys Phe Ile Thr Ile
            660                 665                 670

Phe Gly Thr Arg Ser Val Ser His Leu Arg Lys Val Phe Asp Lys Tyr
        675                 680                 685

Met Thr Ile Ser Gly Phe Gln Ile Glu Glu Thr Ile Asp Arg Glu Thr
    690                 695                 700

Ser Gly Asn Leu Glu Gln Leu Leu Leu Ala Val Val Lys Ser Ile Arg
705                 710                 715                 720

Ser Ile Pro Ala Tyr Leu Ala Glu Thr Leu Tyr Tyr Ala Met Lys Gly
                725                 730                 735

Ala Gly Thr Asp Asp His Thr Leu Ile Arg Val Met Val Ser Arg Ser
            740                 745                 750

Glu Ile Asp Leu Phe Asn Ile Arg Lys Glu Phe Arg Lys Asn Phe Ala
        755                 760                 765

Thr Ser Leu Tyr Ser Met Ile Lys Gly Asp Thr Ser Gly Asp Tyr Lys
    770                 775                 780

Lys Ala Leu Leu Leu Leu Cys Gly Glu Asp Asp Pro Leu Glu His His
785                 790                 795                 800

His His His His


<210> SEQ ID NO 21
<211> LENGTH: 150
<212> TYPE: DNA
<213> ORGANISM: Homo sapiens

<400> SEQUENCE: 21

ggcagcaatg aacttcatca agttccatcg aactgtgact gtctaaatgg aggaacatgt      60

gtgtccaaca agtacttctc caacattcac tggtgcaact gcccaaagaa attcggaggg     120

cagcactgtg aaatagataa gtcaaaaacc                                      150


<210> SEQ ID NO 22
<211> LENGTH: 50
<212> TYPE: PRT
<213> ORGANISM: Homo sapiens

<400> SEQUENCE: 22

Gly Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Lys Ser
        35                  40                  45

Lys Thr
    50


<210> SEQ ID NO 23
```

-continued

```
<211> LENGTH: 4
<212> TYPE: PRT
<213> ORGANISM: Homo sapiens

<400> SEQUENCE: 23

His Trp Gly Phe
1


<210> SEQ ID NO 24
<211> LENGTH: 10
<212> TYPE: PRT
<213> ORGANISM: Homo sapiens

<400> SEQUENCE: 24

Cys Thr Thr His Trp Gly Phe Thr Leu Cys
1               5                   10


<210> SEQ ID NO 25
<211> LENGTH: 35
<212> TYPE: DNA
<213> ORGANISM: Homo sapiens

<400> SEQUENCE: 25

catgccatgg caggcgcttc aggcactaca aatac                                35


<210> SEQ ID NO 26
<211> LENGTH: 34
<212> TYPE: DNA
<213> ORGANISM: Homo sapiens

<400> SEQUENCE: 26

cccaagtctt gggttctctg aattcccctt tctc                                 34


<210> SEQ ID NO 27
<211> LENGTH: 72
<212> TYPE: DNA
<213> ORGANISM: Homo sapiens

<400> SEQUENCE: 27

ggggaattca gagaaggtgg cggttcaggc ggtggaggtt caggaggtgg cggatcaatg     60

gcacaggttc tc                                                         72


<210> SEQ ID NO 28
<211> LENGTH: 66
<212> TYPE: DNA
<213> ORGANISM: Homo sapiens

<400> SEQUENCE: 28

ctttattatt ggaaatcttc aagttcagga gccgcaacag ccaaaacaaa cactaatgag     60

tttttg                                                                66
```